US012797419B2

(12) United States Patent
Murphy et al.

(10) Patent No.: US 12,797,419 B2
(45) Date of Patent: Nov. 17, 2026

(54) AMNIOTIC MEMBRANE HYDROGEL AND METHODS OF MAKING

(71) Applicant: Wake Forest University Health Sciences, Winston-Salem, NC (US)

(72) Inventors: Sean V. Murphy, Winston-Salem, NC (US); Aleksander Skardal, Clemmons, NC (US); Anthony Atala, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 336 days.

(21) Appl. No.: 18/680,930

(22) Filed: May 31, 2024

(65) Prior Publication Data

US 2024/0398873 A1 Dec. 5, 2024

Related U.S. Application Data

(63) Continuation of application No. 18/381,760, filed on Oct. 19, 2023, now abandoned, which is a continuation of application No. 18/118,437, filed on Mar. 7, 2023, now abandoned, which is a continuation of application No. 17/186,278, filed on Feb. 26, 2021, now abandoned, which is a continuation of application No. 16/017,064, filed on Jun. 25, 2018, now Pat. No. 10,967,009, which is a continuation of application No. 14/449,867, filed on Aug. 1, 2014, now Pat. No. 10,016,464, and a continuation of application No. 14/449,705, filed on Aug. 1, 2014, now abandoned, which is a continuation of application No. PCT/US2013/058940, filed on Sep. 10, 2013, said application No. 14/449,867 is a continuation of application No. PCT/US2013/058940, filed on Sep. 10, 2013.

(60) Provisional application No. 61/698,960, filed on Sep. 10, 2012.

(51) Int. Cl.

| | |
|---|---|
| ***A61K 35/50*** | (2015.01) |
| ***A61K 47/36*** | (2006.01) |
| ***A61K 47/42*** | (2017.01) |
| ***A61L 15/40*** | (2006.01) |
| ***A61L 26/00*** | (2006.01) |
| ***A61L 27/34*** | (2006.01) |
| ***A61L 27/36*** | (2006.01) |
| ***A61L 27/48*** | (2006.01) |
| ***A61L 27/52*** | (2006.01) |
| ***C12N 5/00*** | (2006.01) |

(52) U.S. Cl.

CPC .............. *A61K 35/50* (2013.01); *A61K 47/36* (2013.01); *A61K 47/42* (2013.01); *A61L 15/40* (2013.01); *A61L 26/0057* (2013.01); *A61L 26/0076* (2013.01); *A61L 27/34* (2013.01); *A61L 27/3604* (2013.01); *A61L 27/3683* (2013.01); *A61L 27/48* (2013.01); *A61L 27/52* (2013.01); *C12N 5/0068* (2013.01); *A61L 2430/40* (2013.01); *C12N 2533/92* (2013.01)

(58) Field of Classification Search

CPC ........ A61K 35/50; A61K 47/36; A61K 47/42; A61L 15/40; A61L 26/0057; A61L 26/0076; A61L 27/34; A61L 27/3604; A61L 27/3683; A61L 27/48; A61L 27/52; A61L 2430/40; C12N 5/0068; C12N 2533/92

See application file for complete search history.

(56) References Cited

U.S. PATENT DOCUMENTS

| | | | |
|---|---|---|---|
| 4,001,944 | A | 1/1977 | Williams |
| 5,514,378 | A | 5/1996 | Mikos et al. |
| 6,323,219 | B1 | 11/2001 | Costanzo |
| 6,350,463 | B1 | 2/2002 | Herman et al. |
| 7,871,646 | B2 | 1/2011 | Ghinelli et al. |
| 7,968,085 | B2 | 6/2011 | Hersel et al. |
| 8,821,857 | B2 | 9/2014 | Bhatia et al. |
| 8,932,805 | B1 | 1/2015 | Brahm et al. |
| 9,198,939 | B2 | 12/2015 | Tseng et al. |
| 9,526,770 | B2 | 12/2016 | Tseng et al. |

(Continued)

FOREIGN PATENT DOCUMENTS

| | | | |
|---|---|---|---|
| EP | 2708226 | A1 | 3/2014 |
| JP | 2012517235 | A | 8/2012 |

(Continued)

OTHER PUBLICATIONS

Extended European Search Report for European Patent Application No. 13834448.6 issued Jul. 18, 2016.

(Continued)

*Primary Examiner* — Aaron J Kosar

(74) *Attorney, Agent, or Firm* — Saul Ewing LLP; Kathryn Doyle; Justin Crotty

(57) ABSTRACT

The present invention provides compositions and methods for wound healing and tissue regeneration. The compositions of the present invention comprise amniotic membrane of the placenta. In certain embodiments, the composition comprises amniotic membrane powder or solubilized amniotic membrane (SAM). In some aspects, the composition is cell-free and rich in cytokines, extracellular matrix proteins, and other components that improve tissue regeneration. In one aspect, the composition is a hydrogel scaffold that comprises amniotic membrane. The present invention reduces contraction and improves blood vessel development in regenerating tissue.

19 Claims, 13 Drawing Sheets

(56) References Cited

U.S. PATENT DOCUMENTS

| | | | | |
|---|---|---|---|---|
| 9,585,983 | B1 | 3/2017 | Brahm et al. | |
| 10,016,464 | B2 * | 7/2018 | Murphy | A61K 47/36 |
| 10,967,009 | B2 * | 4/2021 | Murphy | A61L 27/48 |
| 2004/0048796 | A1 | 3/2004 | Hariri et al. | |
| 2004/0048798 | A1 | 3/2004 | Raitano et al. | |
| 2005/0220848 | A1 | 10/2005 | Bates | |
| 2007/0003525 | A1 | 1/2007 | Moehlenbruck et al. | |
| 2007/0071740 | A1 | 3/2007 | Tseng et al. | |
| 2008/0039940 | A1 | 2/2008 | Hashimoto et al. | |
| 2008/0108045 | A1 | 5/2008 | Ghinelli et al. | |
| 2008/0306455 | A1 | 12/2008 | Dias et al. | |
| 2009/0280182 | A1 | 11/2009 | Beck et al. | |
| 2010/0055184 | A1 | 3/2010 | Zeitels et al. | |
| 2010/0254900 | A1 | 10/2010 | Campbell et al. | |
| 2011/0189301 | A1 | 8/2011 | Yang et al. | |
| 2011/0206645 | A1 | 8/2011 | Zhang et al. | |
| 2011/0206776 | A1 | 8/2011 | Tom et al. | |
| 2011/0219462 | A1 | 9/2011 | Delbeck et al. | |
| 2012/0077272 | A1 | 3/2012 | Kharazi et al. | |
| 2012/0078378 | A1 | 3/2012 | Daniel et al. | |
| 2012/0189583 | A1 | 7/2012 | Liu et al. | |
| 2013/0006385 | A1 | 1/2013 | Daniel et al. | |
| 2013/0202676 | A1 | 8/2013 | Koob et al. | |
| 2013/0210760 | A1 | 8/2013 | Liu et al. | |
| 2013/0230561 | A1 | 9/2013 | Daniel et al. | |
| 2013/0280344 | A1 | 10/2013 | Tseng et al. | |
| 2014/0051059 | A1 | 2/2014 | Pringle et al. | |
| 2014/0106447 | A1 | 4/2014 | Brown et al. | |
| 2014/0147511 | A1 | 5/2014 | Tseng et al. | |
| 2014/0342015 | A1 | 11/2014 | Murphy et al. | |
| 2015/0342998 | A1 | 12/2015 | Tseng et al. | |
| 2016/0120912 | A1 | 5/2016 | Tseng | |
| 2016/0199417 | A1 | 7/2016 | Werber et al. | |
| 2016/0339061 | A1 | 11/2016 | Tseng et al. | |

FOREIGN PATENT DOCUMENTS

| | | | |
|---|---|---|---|
| JP | 2013536737 | A | 9/2013 |
| WO | 0041732 | A1 | 7/2000 |
| WO | 03024496 | A1 | 3/2003 |
| WO | 2006094247 | A2 | 9/2006 |
| WO | 2007038686 | A2 | 4/2007 |
| WO | 2012170905 | A1 | 12/2012 |
| WO | 2013032938 | A1 | 3/2013 |
| WO | 2013114132 | A1 | 8/2013 |
| WO | 2014040026 | A2 | 3/2014 |
| WO | 2014089440 | A1 | 6/2014 |
| WO | 2016040385 | A1 | 3/2016 |

OTHER PUBLICATIONS

Extended European Search Report for European Patent Application No. 15847740.6 issued May 4, 2018.

PCT International Search Report and Written Opinion for PCT International Application No. PCT/US2015/053571 issued Dec. 28, 2015.

PCT International Search Report and Written Opinion, PCT/US2013/058940, dated Jan. 16, 2014.

Thermo Scientific: Thermo Scientific Hycolne Hystem Hydrogels; Product Packet, Cell Culture & BioProcessing, Logan, UT, 2008, 6 pages.

ESI Bio: Hystem-C Hydrogels; Online URL <http://www.esibio.com/hystem-c-hydrogels/>, Accessed Apr. 27, 2016, 3 pages.

Atala, et al., "Formation of urothelial structures in vivo from dissociated cells attached to biodegradable polymer scaffolds in vitro", J Urol. 148(2 Pt 2), 1992, 658-662.

Atala , et al., "Implantation in vivo and retrieval of artificial structures consisting of rabbit and human urothelium and human bladder muscle", J Urol. 150(2 Pt 2), 1993, 608-612.

Branndon-Peppas , "Preparation and Characterization of Cross-linked Hydrophilic Networks", Absorbent Polymer Technology, Brannon-Peppas and Harland, Eds. 1990, Elsevier: Amsterdam, pp. 45-66.

Burdick , et al., "Hyaluronic acid hydrogels for biomedical applications", Adv Mater. 23(12), Mar. 25, 2011, H41-56, 1-31.

Camci-Unal , et al., "Synthesis and characterization of hybrid hyaluronic acid-gelatin hydrogels", Biomacromolecules, (Apr. 8, 2013), 14(4), 1085-1092.

Cherry , et al., "National Ambulatory Medical Care Survey: 2006 summary", Natl Health Stat Report (3), 2008, 1-39.

Cock, et al., "Pulmonary elastin synthesis and deposition in developing and mature sheep: effects of intrauterine growth restriction", Exp Lung Res. 30(5), 2004, 405-418.

Fedorovich , et al., "Hydrogels as extracellular matrices for skeletal tissue engineering: state-of-the-art and novel application in organ printing", Tissue Eng. 13(8), 2007, 1905-1925.

Hennink , et al., "Novel crosslinking methods to design hydrogels", Adv. Drug Del. Rev. 54, 2002, 13-36.

Hill-West , et al., "Inhibition of thrombosis and intimal thickening by in situ photopolymerization of thin hydrogel barriers", Proc Natl Acad Sci U S A. 91(13), Jun. 21, 1994, 5967-5971.

Hoffman , "Hydrogels for biomedical applications", Adv. Drug Del. Rev. 43, 2002, 3-12.

Hussin , et al., "The Fabrication of Human Amniotic Membrane Based Hydrogel for Cartilage Tissue Engineering Applications: A Preliminary Study", Biomed. IFMBE Proceedings 35, 2011, 841-844.

Hwang , et al., "Chondrogenic Differentiation of Human Embryonic Stem Cell-Derived Cells in Arginine-Glycine-Aspartate-Modified Hydrogels", Tissue Eng. 12, 2006, 26952-706.

Ifkovits , et al., "Review: Photopolymerizable and Degradable Biomaterials for Tissue Engineering Applications", Tissue Eng. 13(10), 2007, 2369-2385.

Katta, et al., "Continuous Electrospinning of Aligned Polymer Nanofibers onto a Wire Drum Collector", Nano Letters 4(11), 2004, 2215-2218.

Kim , et al., "Control of degradation rate and hydrophilicity in electrospun non-woven poly(D,L-lactide) nanofiber scaffolds for biomedical application", Biomaterials. 24(27), 2003, 4977-4985.

Kurd , et al., "Evaluation of the use of prognostic information for the care of individuals with venous leg ulcers or diabetic neuropathic foot ulcers", Wound Repair Regen. 17(3), 2009, 318-325.

Lesher , et al., "Effectiveness of Biobrane for treatment of partial-thickness burns in children", J Pediatr Surg. 46(9), 2011, 1759-1763.

Li , et al., "Collecting Electrospun Nanofibers with Patterned Electrodes", Nano Lett. 5(5), 2005, 913-916.

Li , et al., "Human placenta-derived adherent cells prevent bone loss, stimulate bone formation, and suppress growth of multiple myeloma in bone", Stem Cells. 29(2), Feb. 2011, 263-273.

Miller , et al., "National burn repository 2007 report: a synopsis of the 2007 call for data", J Burn Care Res. 29(6), 2008, 862-870.

Mironov , et al., "Organ printing: computer-aided jet-based 3D tissue engineering", Trends Biotechnol. 21(4), 2003, 157-161.

Nguyen , et al., "Photopolymerizable hydrogels for tissue engineering applications", Biomaterials 23(22), 2002, 4307-4314.

Peck , "Epidemiology of burns throughout the world. Part I: Distribution and risk factors", Burns. 37(7), 2011, 1087-1100.

Peppas , et al., "Preparation Methods and Structure of Hydrogels", Hydrogels in Medicine and Pharmacy, Peppas, Ed. 1986, CRC Press: Boca Raton, Florida, pp. 1-27.

Phelps , et al., "Maleimide Cross-Linked Bioactive PEG Hydrogel Exhibits Improved Reaction Kinetics and Cross-Linking for Cell Encapsulation and In Situ Delivery", Adv. Mater (2012), vol. 24, pp. 64-70.

Pitts , et al., "National Hospital Ambulatory Medical Care Survey: 2006 emergency department summar", Natl Health Stat Report.(7), 2008, 1-38.

Rahmanian-Schwarz , et al., "A clinical evaluation of Biobrane(®) and Suprathel(®) in acute burns and reconstructive surgery", Burns. 37(8), 2011, 1343-1348.

Ratner , et al., "Synthetic Hydrogels for Biomedical Applications", Hydrogels for Medical and Related Applications, Andrade Ed. American Chemical Society: Washington, D.C., 1976, 1-36.

Reading , et al., "Antiviral activity of the long chain pentraxin PTX3 against influenza viruses", J Immunol. 180(5), 2008, 3391-3398.

(56) References Cited

OTHER PUBLICATIONS

Rosen , et al., "Artificial nerve graft using collagen as an extracellular matrix for nerve repair compared with sutured autograft in a rat model", Ann Plast Surg. 25(5), 1990, 375-387.

Sen , et al., "Human skin wounds: a major and snowballing threat to public health and the economy", Wound Repair Regen. 17(6), 2009, 763-771.

Serban , et al., "Synthesis, characterization and chondroprotective properties of a hyaluronan thioethyl ether derivative", Biomaterials. 29(10), 2008, 1388-1399.

Shin , "Biomimetic materials for tissue engineering", Biomaterials 24, 2003, 4353-4364.

Vanderhooft , et al., "Rheological properties of cross-linked hyaluronan-gelatin hydrogels for tissue engineering". Macromol Biosci. 9(1), Jan. 9, 2009, 20-28.

Vanderhooft , et al., "Synthesis and Characterization of Novel Thiol-Reactive Poly(ethylene glycol) Cross-Linkers for Extracellular-Matrix-Mimetic Biomaterials", Biomacromolecules 8, 2007, 2883-2889.

Visconti , et al., "Towards organ printing: engineering an intra-organ branched vascular tree", Expert Opin Biol Ther. 10(3), 2010, 409-420.

Wilshaw, et al., "Production of an Acellular Amniotic Membrane Matrix for Use in Tissue Engineering", Tissue Engineering, Aug. 2006, vol. 12, No. 8, pp. 2117-2129.

Zarembinski , et al., "The Use of a Hydrogel Matrix as a Cellular Delivery Vehicle in Future Cell-Based Therapies: Biological and Non-Biological Considerations", Regenerative Medicine and Tissue Engineering Cells and Biomaterials, 2011.

Zong , "Electrospun fine-textured scaffolds for heart tissue constructs", Biomaterials. 26(26), 2005, 5330-5338.

Zong , et al., "Structure and process relationship of electrospun bioabsorbable nanofiber membranes", Polymer 43(16), 2002, 4403-4412.

* cited by examiner

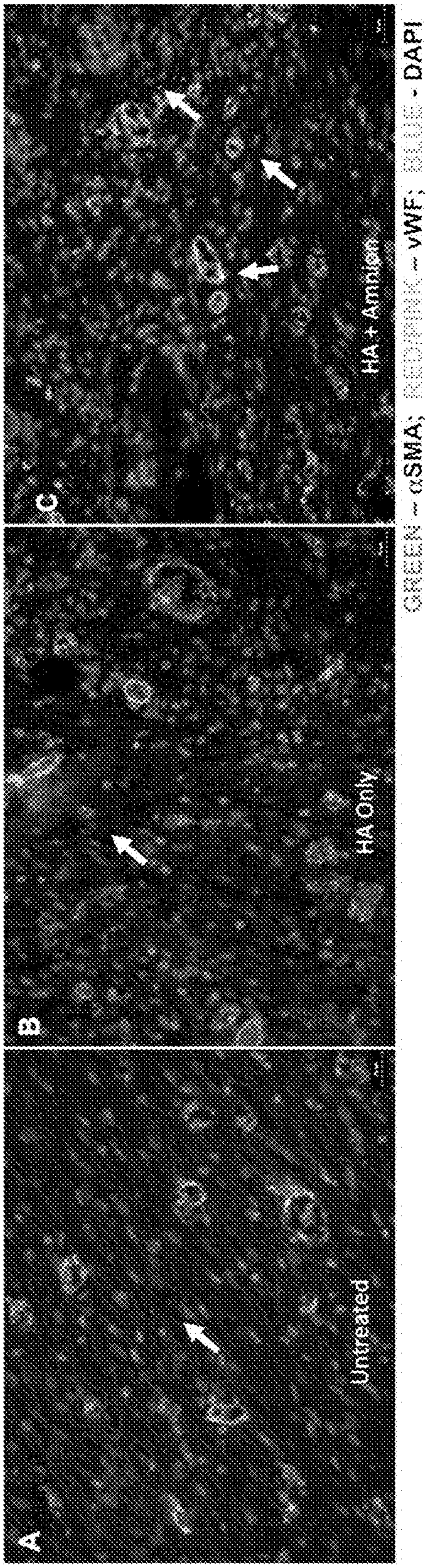
Figure 6A
Figure 6B
Figure 6C
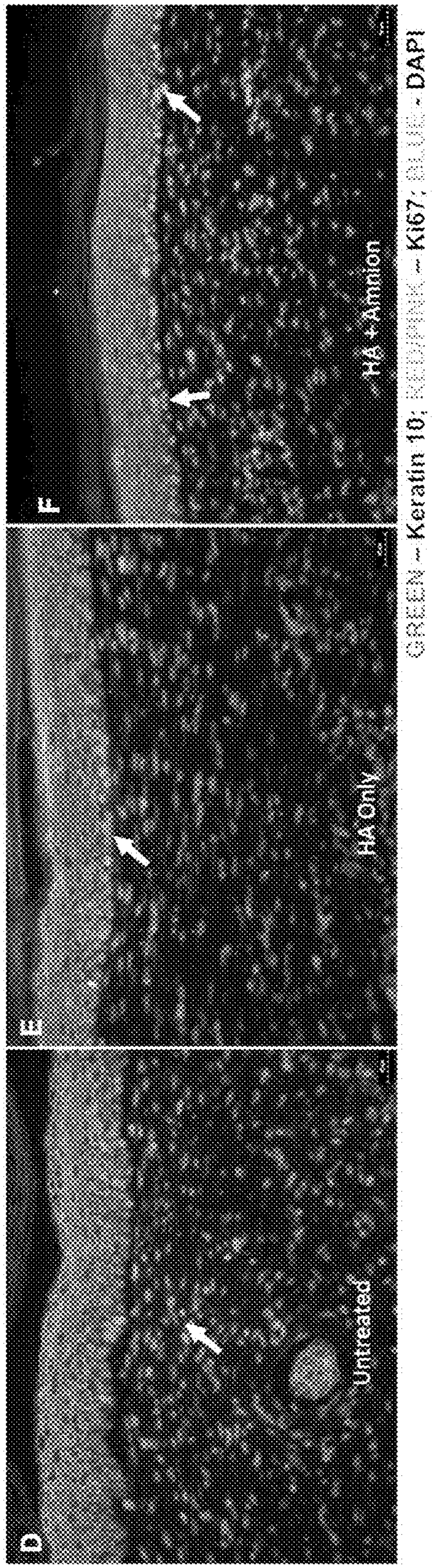
Figure 6D
Figure 6E
Figure 6F

Figure 7
Untreated
Amnion powder
HA gel + amnion
3M Patch
Amniograft
Graftjacket

AMNIOTIC MEMBRANE HYDROGEL AND METHODS OF MAKING

CROSS-REFERENCE TO RELATED APPLICATIONS

The present application is a continuation of U.S. patent application Ser. No. 18/381,760, filed Oct. 19, 2023, which is a continuation of U.S. patent application Ser. No. 18/118,437, filed Mar. 7, 2023, now abandoned, which is a continuation of U.S. patent application Ser. No. 17/186,278, filed Feb. 26, 2021, now abandoned, which is a continuation of U.S. patent application Ser. No. 16/017,064, filed Jun. 25, 2018, now U.S. Pat. No. 10,967,009, which is a continuation of U.S. patent application Ser. No. 14/449,867, filed Aug. 1, 2014, now U.S. Pat. No. 10,016,464, and a continuation of U.S. patent application Ser. No. 14/449,705, filed Aug. 1, 2014, now abandoned, each of which is a continuation of International Application No. PCT/US2013/058940, filed Sep. 10, 2013, which claims the benefit pursuant to 35 U.S.C. § 119(e) of U.S. Provisional Application No. 61/698,960 filed Sep. 10, 2012, all of which applications are incorporated by reference herein in their entireties.

BACKGROUND OF THE INVENTION

Extensive burns and full thickness skin wounds can be devastating to patients, even when treated. There are an estimated 500,000 burns treated in the United States each year (Cherry et al., 2008, Natl Health Stat Report: 1-39; Pitts et al., 2008, Natl Health Stat Report: 1-38). The overall mortality rate for burn injury was 4.9% between 1998-2007 and medical costs for burn treatments approach $2 billion per year (Miller et al., 2008, J Burn Car Res, 29: 862-871). Globally, this statistic increases to 11 million injuries per year (Peck, 2011, Burns, 37: 1087-1100). In addition to burns, full-thickness chronic wounds constitute a large patient base, and despite technological advancement of treatments, healing rates remain below a 50% success rate (Kurd et al., 2009, Wound Repair Regen, 17: 318-325). These non-healing chronic wounds are estimated to effect 7 million people per year in the United States, with yearly costs approaching $25 billion (Sen et al., 2009, Wound Repair Regen, 17: 763-771). Patients who suffer from either of these types of injuries benefit from rapid treatments that result in complete closure and protection of the wounds. In particular, burn patients who receive delayed treatments often are subject to extensive scarring that can result in negative long-term physiological effects.

Recent advances have been made in the treatments of wound healing; however, the gold standard, still employed in the clinic, is an autologous split-thickness skin graft. This involves removing a piece of skin from a secondary surgical site for the patient, stretching the skin, and re-applying the graft on the wound or burn. While this treatment yields a reasonable clinical outcome, if the wound is extensive, then the number and size of donor sites are limited. Allografts are an additional option, are accompanied by the need for immunosuppressive drugs to prevent immune rejection of the graft. These limitations have thus led to the development of non-cellular dermal substitutes, which are most often comprised of a polymeric scaffold. Examples include Integra and Biobrane, and although such materials result in improved wound healing when compared with untreated controls (Lesher et al., 2011, J Pediatr Surg, 46: 1759-1763; Rahmanian et al., 2011, Burns, 37: 1343-1348), they are costly to produce and result in relatively poor cosmetic outcomes.

Recent advances in tissue engineering have led to more complex biological skin equivalents that may yield more suitable wound treatment options for patients. Examples include cellularized graft-like products, such as Dermagraft, Apligraf, and TransCyte. These products are generally comprised of a polymer scaffold patch that is seeded with human fibroblasts and cultured in vitro prior to application. Unfortunately, these grafts are also expensive to produce, and similar to allografts, have the same immunological drawbacks discussed elsewhere herein.

The cell source used in cellular therapies for wound healing is an important consideration which has implications for the cost, speed, and outcome of the treatments. Human keratinocytes are perhaps the optimal cell type to employ. However, autologous and allogenic keratinocytes suffer from the same drawbacks as their autologous and allogenic skin graft counterparts; i.e. secondary surgical sites and potential for rejection, respectively. Furthermore, cell therapies have complicated regulatory and financial hurdles to overcome prior to commercialization.

Thus, there is a need in the art for a wound healing and tissue engineering product that has high clinical efficiency, and that does not require a cellular component, but instead retains the bioactivity of a cellular treatment. The present invention satisfies this unmet need.

SUMMARY OF THE INVENTION

The present invention includes a composition for inducing wound healing and tissue regeneration, where the composition comprises amniotic membrane. In one embodiment, the composition comprises amniotic membrane powder. In one embodiment, the composition comprises solubilized amniotic membrane (SAM).

In one embodiment, the composition is in the form of a powder. In one embodiment, the composition is in the form an ointment. In one embodiment, the composition is in the form an aerosol spray.

In one embodiment the amniotic membrane is derived from a sample of amniotic membrane obtained from a mammal. In one embodiment, the mammal is a human.

In one embodiment, the composition comprises a scaffold. In one embodiment, the scaffold is a hydrogel. In one embodiment, the scaffold comprises at least one biopolymer selected from the group consisting of hyaluronan, chitosan, alginate, collagen, dextran, pectin, carrageenan, polylysine, gelatin and agarose. In one embodiment, the scaffold comprises at least one synthetic polymer selected from the group consisting of (meth)acrylate-oligolactide-PEO-oligolactide-(meth)acrylate, poly(ethylene glycol) (PEO), poly(propylene glycol) (PPO), PEO-PPO-PEO copolymers (Pluronics), poly(phosphazene), poly(methacrylates), poly(N-vinylpyrrolidone), PL(G)A-PEO-PL(G)A copolymers, poly(ethylene imine), and poly(ethyl glycol) diacrylate. In one embodiment, the scaffold comprises a photoinitiator. In one embodiment the at least one biopolymer is thiolated.

The present invention includes a method for making a composition comprising amniotic membrane. The method comprises isolating an amniotic membrane from a mammal; washing the amniotic membrane; lyophilizing the amniotic membrane; and grinding the amniotic membrane to form a powder. In one embodiment, the method further comprises forming a mixture of amniotic membrane powder, pepsin, and a solution; centrifuging the mixture to form a supernatant and a pellet; and removing the supernatant, thereby forming solubilized amniotic membrane (SAM). In one embodiment, the mammal is a human. In one embodiment, the method comprises decellularizing the amniotic membrane.

The present invention includes a method of inducing wound healing and tissue regeneration in a subject comprising administering a composition comprising amniotic membrane to a treatment site in the subject. In one embodiment, the composition comprises amniotic membrane powder. In one embodiment, the composition comprises solubilized amniotic membrane (SAM).

In one embodiment, the composition is in the form of a powder. In one embodiment, the composition is in the form an ointment. In one embodiment, the composition is in the form an aerosol spray.

In one embodiment the amniotic membrane is derived from a sample of amniotic membrane obtained from a mammal. In one embodiment, the mammal is a human.

In one embodiment, the composition comprises a scaffold. In one embodiment, the scaffold is a hydrogel. In one embodiment, the scaffold comprises at least one biopolymer selected from the group consisting of hyaluronan, chitosan, alginate, collagen, dextran, pectin, carrageenan, polylysine, gelatin and agarose. In one embodiment, the scaffold comprises at least one synthetic polymer selected from the group consisting of (meth)acrylate-oligolactide-PEO-oligolactide-(meth)acrylate, poly(ethylene glycol) (PEO), poly(propylene glycol) (PPO), PEO-PPO-PEO copolymers (Pluronics), poly(phosphazene), poly(methacrylates), poly(N-vinylpyrrolidone), PL(G)A-PEO-PL(G)A copolymers, poly(ethylene imine), and poly(ethyl glycol) diacrylate. In one embodiment, the scaffold comprises a photoinitiator. In one embodiment the at least one biopolymer is thiolated.

In one embodiment, the scaffold is bioprinted at the treatment site. In one embodiment, the method comprises administering UV light at the treatment site to induce polymerization of the scaffold.

In one embodiment, the composition is applied directly to the treatment site. In one embodiment, the composition is applied to the surface of a dressing.

In one embodiment, the treatment site is on the external surface of a subject. In one embodiment, the treatment site is at an internal location within the subject.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A illustrates an exemplary method of making SAM derived from human placental tissue. FIG. 1B is a schematic of exemplary materials and methods used in constructing a hydrogel.

FIG. 2A is a graph illustrating the viability of primary keratinocytes in various hydrogels, including hydrogels comprising SAM. FIG. 2B is a graph illustrating the viability of fibroblasts in various hydrogels, including hydrogels comprising SAM.

FIG. 4A is a graph illustrating the percent of wound remaining in each treatment group. FIG. 4B is a graph illustrating the re-epithelialization of wound for each treatment group. FIG. 4C is a graph illustrating the percent of contracture in each treatment group. FIG. 4D is a graph illustrating the wound aspect ratio in each treatment group.

FIG. 5A through FIG. 5C are a set of images depicting H&E staining of the wound areas demonstrating blood vessels present in regenerating tissue of untreated (FIG. 5A), HA-hydrogel treated (FIG. 5B), and HA-hydrogel comprising SAM treated (FIG. 5C) wounds. FIG. 5D is a graph illustrating the quantification of blood vessel density in untreated wounds, wounds treated with HA-hydrogel, and wounds treated with HA-hydrogel+SAM. FIG. 5E is a graph illustrating the quantification of blood vessel size in untreated wounds, wounds treated with HA-hydrogel, and wounds treated with HA-hydrogel+SAM. FIG. 5F is a graph illustrating the distribution of blood vessel size (large, medium, or small) in untreated wounds, wounds treated with HA-hydrogel, and wounds treated with HA-hydrogel+SAM.

FIGS. 6A-6F are a set of images illustrating the results of experiments. FIG. 6A through FIG. 6C are images depicting the staining for von willebrand factor and α-smooth muscle actin in regenerating tissue of untreated (FIG. 6A), HA-hydrogel treated (FIG. 6B), and HA-hydrogel comprising SAM treated (FIG. 6C) wounds. FIG. 6D through FIG. 6F are images depicting the staining for keratin 10 and Ki67 in regenerating tissue of untreated (FIG. 6D), HA-hydrogel treated (FIG. 6E), and HA-hydrogel comprising SAM treated (FIG. 6F) wounds.

FIG. 8A is a graph illustrating the skin thickness in untreated wounds, wounds treated with HA-hydrogel, and wounds treated with HA-hydrogel+SAM. FIG. 8B is a graph illustrating cell proliferation, as measured by the number of Ki67+ cells per area, in untreated wounds, wounds treated with HA-hydrogel, and wounds treated with HA-hydrogel+SAM.

FIG. 9A is a graph illustrating hydrogel swelling of HA only and HA-SAM hydrogels over 24 hours. FIG. 9B is a graph illustrating cumulative protein release over 14 hours. FIG. 9C is a graph illustrating the fit of a first order release model, indicative of concentration dependent protein release, to the observed protein release. FIG. 9D is a graph illustrating the fit of the Hixson-Crowell release model, indicative of hydrogel breakdown, to the observed protein release. FIG. 9E is a graph illustrating the fit of the Higuchi release model, indicative of diffusion mediated protein release, to the observed protein release.

DETAILED DESCRIPTION

Figure 1A:
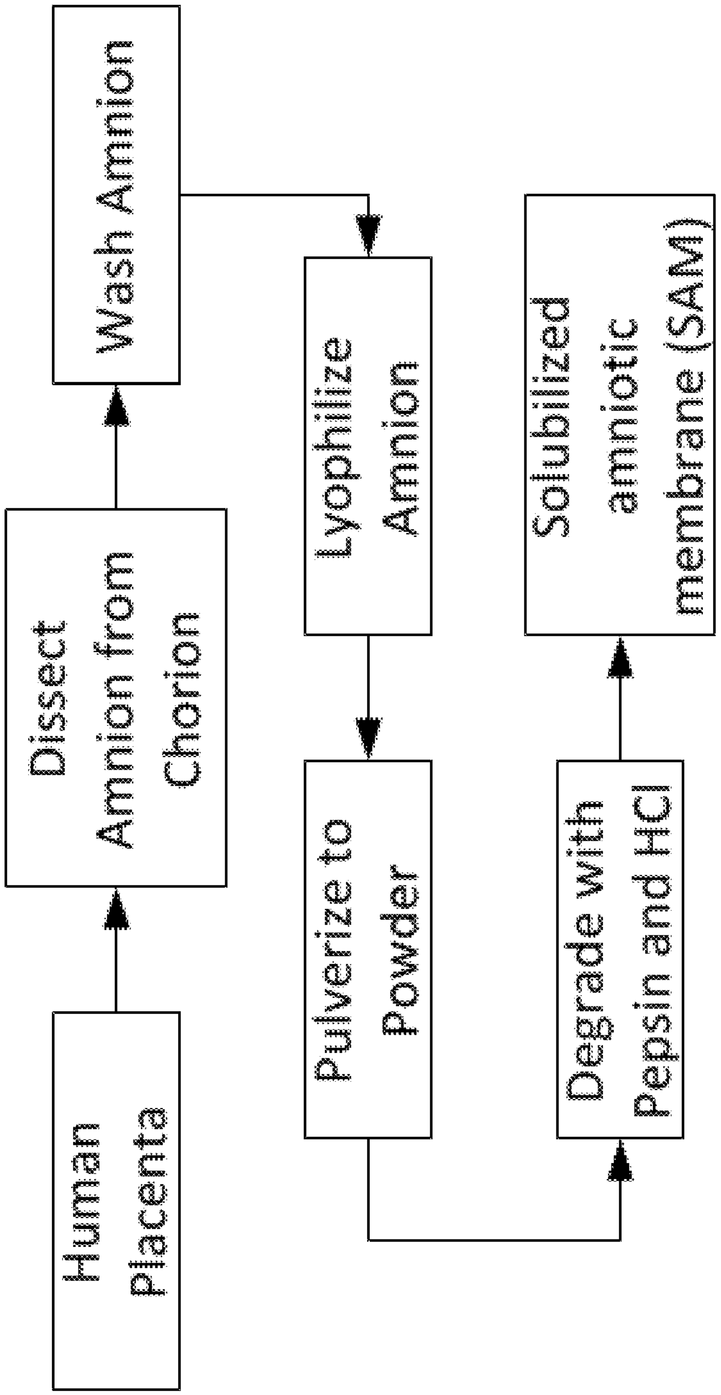
FIGS. 1A-1B depict schematic illustrations of exemplary methods to construct embodiments of the present invention.

The present invention relates generally to compositions and methods for inducing wound healing and tissue regeneration. In one embodiment, the present invention provides compositions, and methods of making the same, comprising amniotic membrane. In one embodiment, the composition comprises cytokines, extracellular matrix proteins, and other components that improve wound healing and tissue regeneration.

In one embodiment, the composition of the invention is cell-free, thereby minimizing potential inflammatory responses. The wound healing product of the invention has high clinical efficiency without requiring a cellular component, yet the wound healing product of the invention retains the bioactivity of a cellular treatment. In one embodiment the composition comprises amniotic membrane powder. In one embodiment, the composition comprises solubilized amniotic membrane (SAM).

In one embodiment, the present invention provides methods of applying an amniotic membrane-containing composition to a subject to induce wound healing. For example, in one embodiment, the composition is applied directly to a wound in a subject. In certain embodiments, the composition is applied as an aerosol spray, gel, cream, or ointment.

In one embodiment, the present invention relates to a method of making the amniotic membrane-containing composition. The method of the invention comprises isolating the amniotic membrane from the placenta of a mammal. In one embodiment, the method comprises lyophilizing the amniotic membrane. In another embodiment, the method comprises forming a powder from the amniotic membrane. In one embodiment, the method comprises solubilizing the powder to form SAM. In one embodiment, the mammal is a human.

In one embodiment, the present invention provides an amniotic membrane-based tissue engineering scaffold, and methods of making the same. In one embodiment, the scaffold is a hydrogel, wherein amniotic membrane or SAM is incorporated within the hydrogel. In another embodiment amniotic membrane or SAM is applied to a scaffold. In one embodiment the amniotic membrane-based scaffold of the invention enhances tissue regeneration. In one embodiment, the amniotic membrane-based scaffold of the invention reduces tissue contraction. In one embodiment the amniotic membrane-based scaffold enhances blood vessel development in regenerating tissue.

In one embodiment, the present invention provides methods of promoting tissue regeneration in a subject comprising administering to the subject a amniotic membrane-based scaffold. In one embodiment, the method comprises bioprinting of a amniotic membrane-based hydrogel at a site in need of tissue regeneration in a subject. In one embodiment, the method comprises initiating polymerization of the hydrogel after application to the site. In one embodiment, the method comprises photo-crosslinking of the amniotic membrane-based hydrogel. In another embodiment, amniotic membrane or SAM is incorporated within a hyaluronic acid (HA)-based hydrogel that, in certain instances is bioprinted over wounds and photocrosslinked in place.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

As used here, "biocompatible" refers to any material, which, when implanted in a mammal, does not provoke an adverse response in the mammal. A biocompatible material, when introduced into an individual, is not toxic or injurious to that individual, nor does it induce immunological rejection of the material in the mammal.

As used herein, a "culture," refers to the cultivation or growth of cells, for example, tissue cells, in or on a nutrient medium. As is well known to those of skill in the art of cell or tissue culture, a cell culture is generally begun by removing cells or tissue from a human or other animal, dissociating the cells by treating them with an enzyme, and spreading a suspension of the resulting cells out on a flat surface, such as the bottom of a Petri dish. There the cells generally form a thin layer of cells called a "monolayer" by producing glycoprotein-like material that causes the cells to adhere to the plastic or glass of the Petri dish. A layer of culture medium, containing nutrients suitable for cell growth, is then placed on top of the monolayer, and the culture is incubated to promote the growth of the cells.

The term "decellularized" or "decellularization" as used herein refers to a biostructure (e.g., an organ, or part of an organ), from which the cellular and tissue content has been removed leaving behind an intact acellular infra-structure. Organs such as the kidney are composed of various specialized tissues. The specialized tissue structures of an organ, or parenchyma, provide the specific function associated with the organ. The supporting fibrous network of the organ is the stroma. Most organs have a stromal framework composed of unspecialized connecting tissue which supports the specialized tissue. The process of decellularization removes the specialized tissue, leaving behind the complex three-dimensional network of connective tissue. The connective tissue infra-structure is primarily composed of collagen. The decellularized structure provides a biocompatible substrate onto which different cell populations can be infused. Decellularized biostructures may be rigid, or semi-rigid, having an ability to alter their shapes. Examples of decellularized organs useful in aspects of the present invention include, but are not limited to, the heart, kidney, liver, pancreas, spleen, bladder, ureter and urethra, cartilage, bone, brain, spine cord, peripheral nerve.

The term "derived from" is used herein to mean to originate from a specified source.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

An "effective amount" or "therapeutically effective amount" of a compound is that amount of compound which is sufficient to provide a beneficial effect to the subject to which the compound is administered. An "effective amount" of a delivery vehicle is that amount sufficient to effectively bind or deliver a compound.

As used herein "endogenous" refers to any material from or produced inside an organism, cell or system.

"Exogenous" refers to any material introduced from or produced outside an organism, cell, or system.

As used herein, "extracellular matrix composition" includes both soluble and non-soluble fractions or any portion thereof. The non-soluble fraction includes those secreted ECM proteins and biological components that are deposited on the support or scaffold. The soluble fraction includes refers to culture media in which cells have been cultured and into which the cells have secreted active agent(s) and includes those proteins and biological components not deposited on the scaffold. Both fractions may be collected, and optionally further processed, and used individually or in combination in a variety of applications as described herein.

As used herein, the term "gel" refers to a three-dimensional polymeric structure that itself is insoluble in a particular liquid but which is capable of absorbing and retaining large quantities of the liquid to form a stable, often soft and pliable, but always to one degree or another shape-retentive, structure. When the liquid is water, the gel is referred to as a hydrogel. Unless expressly stated otherwise, the term "gel" will be used throughout this application to refer both to polymeric structures that have absorbed a liquid other than water and to polymeric structures that have absorbed water, it being readily apparent to those skilled in the art from the context whether the polymeric structure is simply a "gel" or a "hydrogel."

As used herein, a "graft" refers to a cell, tissue or organ that is implanted into an individual, typically to replace, correct or otherwise overcome a defect. A graft may further comprise a scaffold. The tissue or organ may consist of cells that originate from the same individual; this graft is referred to herein by the following interchangeable terms: "autograft", "autologous transplant", "autologous implant" and "autologous graft". A graft comprising cells from a genetically different individual of the same species is referred to herein by the following interchangeable terms: "allograft," "allogeneic transplant," "allogeneic implant," and "allogeneic graft." A graft from an individual to his identical twin is referred to herein as an "isograft," a "syngeneic transplant," a "syngeneic implant" or a "syngeneic graft." A "xenograft," "xenogeneic transplant," or "xenogeneic implant" refers to a graft from one individual to another of a different species.

As used herein "growth factors" is intended the following non-limiting factors including, but not limited to, growth hormone, erythropoietin, thrombopoietin, interleukin 3, interleukin 6, interleukin 7, macrophage colony stimulating factor, c-kit ligand/stem cell factor, osteoprotegerin ligand, insulin, insulin like growth factors, epidermal growth factor (EGF), fibroblast growth factor (FGF), nerve growth factor, ciliary neurotrophic factor, platelet derived growth factor (PDGF), transforming growth factor (TGF-beta), hepatocyte growth factor (HGF), and bone morphogenetic protein at concentrations of between picogram/ml to milligram/ml levels.

"Native cells," as used herein means cells that are native, resident, or endogenous to the placental membrane, i.e. cells that are not exogenously added to the placental membrane.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a mammal, and in other embodiments, the mammal is a human.

"Photo-crosslinking" refers to bond formation that links one polymer chain to another upon exposure to light of appropriate wavelengths. For example, two polymers conjugated to a photoreactive group may be covalently photo-crosslinked by covalent bond formation between the photoreactive groups.

A "photoinitiator" typically includes an agent that forms free radicals when illuminated by light of appropriate wavelengths. Non-limiting example classes of compounds useful as photoinitiators include aromatic carbonyl compounds (e.g., benzoin derivatives, benziketals, acetophenone derivatives, hydroxyalkylphenones) and aromatic ketones (e.g., benzophenone and thioxanthone). Non-limiting examples of photoinitiators include Esacure from Lamberti spa, benzophenone, dimethoxyphenyl acetophenone, 2,2-dimethoxy, 2-phenylacetophenone and 2,2-diethoxyacetophenone, 1-[4-(2-hydroxyethoxy)-phenyl]-2-hydroxy-2-methyl-1-propane-1-one, ethyl eosin, eosin Y, fluorescein, 2,2-dimethoxy, 2-phenylacetophenone, 2-methyl, 2-phenylacetonphenone, 12959, camphorquinone, rose bengal, methylene blue, erythosin, phloxime, thionine, riboflavin, and methyl green. Still other photoinitiators comprise 1-(4-Fluorphenyl)-2-methyl-2-morpholino-1-propanone, 1,7-bis(9-acridinyl) heptane, 1-Chloro-4-propoxythioxanthone, 1-Hydroxy cyclohexyl phenyl ketone, 2,2-Di ethoxy acetophenone, 2,3,4,4'-Tetrahydroxy Benzophenone, 2,3,4-Trihydroxybenzophenone, 2,4,6-Trimethyl benzoyl diphenyl phosphine oxide, 2,4,6-Trimethylbenzophenone, 2/4-Diethylthioxanthone, 2/4-Isopropylthioxanthone, 2-Benzyl-2-(dimethylamino)-1-[4-(4-morpholinyl)phenyl]-1-butanone, 2-Chlorothioxanthone, 2-Dimethyl-aminoethylbenzoate, 2-Ethylhexyl-4-dimethylaminobenzoate, 2-Hydroxy-2-methyl-phenyl-propan-1-one, 2-Hydroxy-4'-hydroxyethoxy-2-methylpropiophenone, 2-Isopropylthioxanthone, 2-Methyl Benzophenone, 2-Methyl-1-[4-(methylthio)phenyl]-2-morpholinopropanone-1,4-(4-Methylphen-ylthiophenyl)-phenylmethanone, 4,4'-Difluoro benzophenone, 4,4'-Dimethoxy benzophenone, 4-Chloro benzophenone, 4-Methyl acetophenone, 4-Methyl benzophenone, 4-Phenylbenzophenone, Benzil dimethyl ketal, Benzophenone, Benzophenone hydrazone, Bis(p-tolyl) iodonium hexafluorophosphate, Dimethyl Sebacate, Diphenyl Iodonium Hexafluorophosphate, Ethyl (2,4,6-trimethylbenzoyl)phenylphosphinate, Ethyl-4-(dimethylamino)benzoate, Methyl o-benzoyl benzoate, Methyl phenyl glyoxylate, N,N,N',N'-Tetraethyl-4,4-diaminobenzophenone, Phenyltribromomethylsulphone, acylphosphine oxide (APO) and bisacylphosphine oxide (BAPO), 1-[4-(2-Hydroxyethoxy)-phenyl]-2-hydroxy-2-methyl-1-propane-1-one, 2,2-Dimethoxy-1,2-diphenylethan-1-one, hydroxy-cyclohexyl-phenyl-ketone, methylbenzoylformate, oxy-phenyl-acetic acid 2-[2 oxo-2 phenyl-acetoxy-ethoxy] ethyl ester, oxy-phenyl-acetic2-[2-hydroxy-ethoxy]-ethyl ester, alpha-dimethoxy-alpha-phenylacetophenone, 2-Benzyl-2-(dimethyl-amino)-1-[4-(4-morpholinyl)phenyl]-1-butanone, diphenyl (2,4,6-trimethylbenzoyl)-phosphine oxide, phosphine oxide, bis(eta 5-2,4-cyclopentadien-1-yl), bis[2,6-difluoro-3-(1H-pyrrol-1-yl)phenyl]titanium, Iodonium, (4-methylphenyl) [4-(2-methylpropyl)phenyl]-hexafluorophosphate(1-), bis(2,6-dimethoxybenzoyl)-2,4,4-trimethyl pentylphosphineoxide. Photoinitiators also comprise related compounds and derivatives of these compounds.

"Proliferation" is used herein to refer to the reproduction or multiplication of similar forms, especially of cells. That is, proliferation encompasses production of a greater number of cells, and may be measured by, among other things, simply counting the numbers of cells, measuring incorporation of $^3$H-thymidine into the cell, and the like.

"Progression of or through the cell cycle" is used herein to refer to the process by which a cell prepares for and/or enters mitosis and/or meiosis. Progression through the cell cycle includes progression through the G1 phase, the S phase, the G2 phase, and the M-phase.

As used herein, "scaffold" refers to a structure, comprising a biocompatible material that provides a surface suitable for adherence and proliferation of cells. A scaffold may further provide mechanical stability and support. A scaffold may be in a particular shape or form so as to influence or delimit a three-dimensional shape or form assumed by a population of proliferating cells. Such shapes or forms include, but are not limited to, films (e.g. a form with two-dimensions substantially greater than the third dimension), ribbons, cords, sheets, flat discs, cylinders, spheres, 3-dimensional amorphous shapes, etc.

As used herein, a "substantially purified" component is a component that is essentially free of other components. Thus, a substantially purified cell refers to a cell which has been purified from other cell types with which it is normally associated in its naturally-occurring state.

A "therapeutic" treatment is a treatment administered to a subject who exhibits signs of pathology, for the purpose of diminishing or eliminating those signs.

As used herein, "treating a disease or disorder" means reducing the frequency with which a symptom of the disease or disorder is experienced by a patient. Disease and disorder are used interchangeably herein.

As used herein, "tissue engineering" refers to the process of generating a tissue ex vivo for use in tissue replacement or reconstruction. Tissue engineering is an example of "regenerative medicine," which encompasses approaches to the repair or replacement of tissues and organs by incorporation of cells, gene or other biological building blocks, along with bioengineered materials and technologies.

As used herein, the terms "tissue grafting" and "tissue reconstructing" both refer to implanting a graft into an individual to treat or alleviate a tissue defect, such as a lung defect or a soft tissue defect.

"Transplant" refers to a biocompatible lattice or a donor tissue, organ or cell, to be transplanted. An example of a transplant may include but is not limited to skin cells or tissue, bone marrow, and solid organs such as heart, pancreas, kidney, lung and liver.

The term "wound" as used herein refers to all types of tissue injuries, including those inflicted by surgery and trauma, including burns, as well as injuries from chronic medical conditions, such as atherosclerosis, vascular disease, or diabetes. The compositions described herein are useful for treatment of all types of wounds, including wounds to internal and external tissues. The wound dressings are intended to treat the various etiologies of wounds that affect the three layers of the skin (i.e., the epidermis, dermis, and subcutaneous layers).

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention provides compositions and methods for use in wound healing and tissue regeneration. The invention is now described in particular detail.

Composition

The present invention provides a composition comprising amniotic membrane for use in wound healing and tissue regeneration applications. The amniotic membrane, or amnion, is a thin tissue that forms the wall of the amniotic sac. During pregnancy, the amniotic membrane surrounds and protects a developing embryo. The amniotic membrane comprises a thick basement membrane and an avascular stromal matrix. Patches of amniotic membrane have been implemented as dressings for skin wounds, as the amniotic membrane is believed to contain components that aid in wound healing.

In one embodiment, the composition is cell-free. In one embodiment, the composition comprises cytokines, extracellular matrix (ECM) proteins, ECM-associated proteins, and other factors known to promote wound healing. In one embodiment, the composition modulates inflammatory responses.

The present invention further provides methods of making the composition. In one embodiment, the method of the invention comprises isolating the amniotic membrane from a placenta of a mammal, for example a human. In some instances, it is beneficial for the amniotic membrane to be obtained from the same species as the subject who will eventually be treated with the derived amniotic membrane-based product. In one embodiment, the amniotic membrane is separated from the chorion membrane. As would be understood by those skilled in the art, any method of separation or dissection of the amniotic membrane from the rest of the placenta may be used. In one embodiment, the method comprises removing any blood or blood clots from the isolated membrane. In one embodiment, the method comprises washing the membrane. The membrane may be washed or rinsed in any suitable solution. For example, in one embodiment, the membrane is washed in sterile water. In another embodiment, the membrane is washed in sterile saline. In another embodiment, the membrane is washed in suitable cell culture media.

In one embodiment, the amniotic membrane is decellularized using any method of decellularization known in the art. In an exemplary method, the decellularization process comprises a series of sequential extractions. One feature of this extraction process is that harsh extraction that may disturb or destroy the complex infra-structure of the bio-structure, can be avoided. The first step involves removal of cellular debris and solubilization of the cell membrane. This is followed by solubilization of the nuclear cytoplasmic components and the nuclear components.

In one embodiment, the membrane is decellularized by removing the cell membrane and cellular debris surrounding the organ using gentle mechanical disruption methods. The gentle mechanical disruption methods must be sufficient to disrupt the cellular membrane, while avoiding damaging or disturbing the membrane's complex infra-structure. Gentle mechanical disruption methods include scraping the surface of the membrane, agitating the membrane, or stirring the membrane in a suitable volume of fluid, e.g., distilled water. In one embodiment, the gentle mechanical disruption method includes magnetically stirring (e.g., using a magnetic stir bar and a magnetic plate) the membrane in a suitable volume of distilled water until the cell membrane is disrupted and the cellular debris has been removed from the membrane.

In another embodiment, the amniotic membrane is not decellularized. In some aspects, it may be beneficial to not decellularize the amniotic membrane. While not wishing to be bound by any particular theory, it is believed that decellularizing the amniotic membrane may remove various components of the membrane which are important for wound healing applications. Thus, while the present invention is not limited by whether the amniotic membrane is or is not decellularized, the eventual use for the produced composition may dictate whether or not to include a decellularization step in the present method. Further, in some instances, it is beneficial to only partially decellularize the membrane.

In one embodiment, the method comprises lyophilizing the amniotic membrane. Lyophilization, or freeze-dying, of the amniotic membrane may be carried out by any method known in the art; see, e.g., U.S. Pat. No. 4,001,944. For example, the membrane may be quickly frozen in 100% ethanol and dry ice, then lyophilized at −20° C. in a sterile lyophilizer until dry.

In one embodiment of the method of the present invention, the amniotic membrane is cut into pieces. The membrane may be cut using a pair of scissors, a knife, a pair of forceps, a scalpel, a microtome, and the like. In another embodiment, the amniotic membrane is milled, minced, or grounded into a fine powder. Formation of the amniotic membrane derived powder may be carried out by any method known in the art. For example, in one embodiment, membrane pieces are placed within a cryogenic impact grinder. An exemplary cryogenic impact grinder is the Spex SamplePrep 6870 Freezer/Mill®, which allows for cycling of cooling phases and milling phases during the grinding of samples.

In one embodiment, the membrane is further digested. For example, in one embodiment, powderized amniotic membrane is co-incubated with pepsin in a suitable solution. In one embodiment, the solution is HCl. In one embodiment, the digest is centrifuged, where the supernatant is removed thereby forming the SAM of the present invention. In some instances, the pH of the SAM is adjusted. In one embodiment, the pH of the SAM is adjusted to a pH of about 7. SAM may be stored at suitable temperature until required for use. In some embodiments, the SAM may be mixed with a suitable isotonic buffer or cell culture medium. Suitable buffers include, but are not limited to, phosphate buffered saline (PBS), saline, MOPS, HEPES, Hank's Balanced Salt Solution, and the like. A suitable cell culture medium includes, but is not limited to, RPMI 1640, Fisher's, Iscove's, McCoy's, Dulbecco's medium, and the like. In certain embodiments, the present invention includes an amniotic membrane powder, which in certain instances may be combined with a suitable buffer. That is, in certain embodiments, the composition of the present invention comprises amniotic membrane powder. In one embodiment, the composition comprises SAM. In certain embodiments, the composition comprises a cream, liquid, gel, spray, ointment, or the like which comprises the amniotic membrane powder or SAM described herein.

The present invention also provides pharmaceutical compositions comprising amniotic membrane. As described elsewhere herein, the present invention is based upon the finding that amniotic membrane enhances wound healing and tissue regeneration. Formulations may be employed in admixtures with conventional excipients, i.e., pharmaceutically acceptable organic or inorganic carrier substances suitable for administration to the wound or treatment site. The pharmaceutical compositions may be sterilized and if desired mixed with auxiliary agents, e.g., lubricants, preservatives, stabilizers, wetting agents, emulsifiers, salts for influencing osmotic pressure buffers, coloring, and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, PA), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

In an embodiment, the composition includes an antioxidant and a chelating agent that inhibits the degradation of one or more components of SAM. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of SAM in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid.

Liquid solutions of SAM in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

In certain instances, one benefit of the composition of the present invention is that it has the ability to fill irregular and deep wounds. Thus, in one embodiment, the pharmaceutical composition may be topically applied to a wound or to a site in need of tissue regeneration.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see U.S. Pat. No. 6,323,219).

In alternative embodiments, the formulations suitable for topical administration may be optionally combined with other ingredients such as adjuvants, anti-oxidants, chelating agents, surfactants, foaming agents, wetting agents, emulsifying agents, viscosifiers, buffering agents, preservatives, and the like. In another embodiment, a permeation or penetration enhancer is included in the composition and is effective in improving the percutaneous penetration of the amniotic membrane components into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents, such as isopropyl alcohol, propylene glycol, or sodium xylene sulfonate, are known to those of skill in the art.

Formulations suitable for topical administration should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. More preferable, it should be present in an amount from about 0.0005% to about 5% of the composition; most preferably, it should be present in an amount of from about 0.001% to about 1% of the composition. Such compounds may be synthetically- or naturally derived.

In another embodiment, the pharmaceutical composition comprising amniotic membrane powder or SAM may be applied to a bandage or dressing, which is then applied to the wound or treatment site of a subject. For example, in one embodiment, a dressing is soaked in a liquid solution or liquid suspension comprising amniotic membrane powder or SAM. In another embodiment, an ointment comprising amniotic membrane powder or SAM is applied to a surface of a dressing or bandage.

In another embodiment, the pharmaceutical composition comprises an aerosolized or atomized solution or suspension comprising amniotic membrane powder or SAM. Such aerosolized, or aerosolized formulations, when dispersed, preferably have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but which are known to those of skill in the art.

Amniotic Membrane-Based Scaffolds

The present invention provides a amniotic membrane-based tissue engineering scaffold useful in wound healing and tissue regeneration. For example, in one embodiment, amniotic membrane powder or SAM is incorporated within a scaffold. In another embodiment, amniotic membrane powder or SAM is applied to the surface of a scaffold. The scaffold of the invention may be of any type known in the art. Non-limiting examples of such a scaffold includes a, hydrogel, electrospun scaffold, foam, mesh, sheet, patch, and sponge.

In one embodiment, the scaffold may comprise any polysaccharide, including glycosaminoglycans (GAGs) or glucosaminoglycans, with suitable viscosity, molecular mass and other desirable properties. By glycosaminoglycan is intended any glycan (i.e., polysaccharide) comprising an unbranched polysaccharide chain with a repeating disaccharide unit, one of which is always an amino sugar. These compounds as a class carry a high negative charge, are strongly hydrophilic, and are commonly called mucopolysaccharides. This group of polysaccharides includes heparin, heparan sulfate, chondroitin sulfate, dermatan sulfate, keratan sulfate, and hyaluronic acid. These GAGs are predominantly found on cell surfaces and in the extracellular matrix. By glucosaminoglycan is also intended any glycan (i.e. polysaccharide) containing predominantly monosaccharide derivatives in which an alcoholic hydroxyl group has been replaced by an amino group or other functional group such as sulfate or phosphate. An example of a glucosaminoglycan is poly-N-acetyl glucosaminoglycan, commonly referred to as chitosan. Exemplary polysaccharides that may be useful in the present invention include dextran, heparan, heparin, hyaluronic acid, alginate, agarose, carageenan, amylopectin, amylose, glycogen, starch, cellulose, chitin, chitosan and various sulfated polysaccharides such as heparan sulfate, chondroitin sulfate, dextran sulfate, dermatan sulfate, or keratan sulfate.

(a) Hydrogels

In one embodiment, the present invention provides a hydrogel comprising amniotic membrane powder or SAM. Hydrogels can generally absorb a great deal of fluid and, at equilibrium, typically are composed of 60-90% fluid and only 10-30% polymer. In a preferred embodiment, the water content of hydrogel is about 70-80%. Hydrogels are particularly useful due to the inherent biocompatibility of the cross-linked polymeric network (Hill-West, et al., 1994, Proc. Natl. Acad. Sci. USA 91:5967-5971). Hydrogel biocompatibility may be attributed to hydrophilicity and ability to imbibe large amounts of biological fluids (Brannon-Peppas. Preparation and Characterization of Cross-linked Hydrophilic Networks in Absorbent Polymer Technology, Brannon-Peppas and Harland, Eds. 1990, Elsevier: Amsterdam, pp 45-66; Peppas and Mikos. Preparation Methods and Structure of Hydrogels in Hydrogels in Medicine and Pharmacy, Peppas, Ed. 1986, CRC Press: Boca Raton, Fla., pp 1-27). The hydrogels may be prepared by crosslinking hydrophilic biopolymers or synthetic polymers. Examples of the hydrogels formed from physical or chemical crosslinking of hydrophilic biopolymers, include but are not limited to, hyaluronans, chitosans, alginates, collagen, dextran, pectin, carrageenan, polylysine, gelatin or agarose. (see.: W. E. Hennink and C. F. van Nostrum, 2002, Adv. Drug Del. Rev. 54, 13-36 and A. S. Hoffman, 2002, Adv. Drug Del. Rev. 43, 3-12). These materials consist of high-molecular weight backbone chains made of linear or branched polysaccharides or polypeptides. Examples of hydrogels based on chemical or physical crosslinking synthetic polymers include but are not limited to (meth)acrylate-oligolactide-PEO-oligolactide-(meth)acrylate, poly(ethylene glycol) (PEO), poly(propylene glycol) (PPO), PEO-PPO-PEO copolymers (Pluronics), poly(phosphazene), poly(methacrylates), poly(N-vinylpyrrolidone), PL(G)A-PEO-PL(G)A copolymers, poly(ethylene imine), etc. (see A. S Hoffman, 2002Adv. Drug Del. Rev, 43, 3-12). In some embodiments, the hydrogel comprises poly (ethylene glycol) diacrylate (PEGDA).

In one embodiment, the hydrogel comprises at least one biopolymer. In other embodiments, the hydrogel scaffold further comprises at least two biopolymers. In yet other embodiments, the hydrogel scaffold further comprises at least one biopolymer and at least one synthetic polymer. In one embodiment, the hydrogel of the present invention comprises hyaluronic acid, gelatin, and PEGDA.

In one embodiment, components of the hydrogel of the invention are modified. For example, in one embodiment, monomers may be modified with methacrylic anhydride (MA). In another embodiment, components of the hydrogel are modified with thiol-ene photopolymerization chemistry to produce thiolated components. For example, in one embodiment, the hydrogel comprises thiolated hyaluronic acid and thiolated gelatin.

Hydrogels closely resemble the natural living extracellular matrix (Ratner and Hoffman. Synthetic Hydrogels for Biomedical Applications in Hydrogels for Medical and Related Applications, Andrade, Ed. 1976, American Chemical Society: Washington, D.C., pp 1-36). Hydrogels may also be made degradable in vivo by incorporating PLA, PLGA or PGA polymers. Moreover, hydrogels may be modified with fibronectin, laminin, vitronectin, or, for example, RGD for surface modification, which may promote cell adhesion and proliferation (Heungsoo Shin, 2003, Biomaterials 24:4353-4364; Hwang et al., 2006 Tissue Eng. 12:2695-706). Indeed, altering molecular weights, block structures, degradable linkages, and cross-linking modes may influence strength, elasticity, and degradation properties of the instant hydrogels (Nguyen and West, 2002, Biomaterials 23(22):4307-14; Ifkovits and Burkick, 2007, Tissue Eng. 13(10):2369-85).

Hydrogels may also be modified with functional groups for covalently attaching a variety of proteins (e.g., collagen) or compounds such as therapeutic agents. Therapeutic agents which may be linked to the matrix include, but are not limited to, analgesics, anesthetics, antifungals, antibiotics, anti-inflammatories, anthelmintics, antidotes, antiemetics, antihistamines, antihypertensives, antimalarials, antimicrobials, antipsychotics, antipyretics, antiseptics, antiarthritics, antituberculotics, antitussives, antivirals, cardioactive drugs, cathartics, chemotherapeutic agents, a colored or fluorescent imaging agent, corticoids (such as steroids), antidepressants, depressants, diagnostic aids, diuretics, enzymes, expectorants, hormones, hypnotics, minerals, nutritional supplements, parasympathomimetics, potassium supplements, radiation sensitizers, a radioisotope, sedatives, sulfonamides, stimulants, sympathomimetics, tranquilizers, urinary anti-infectives, vasoconstrictors, vasodilators, vitamins, xanthine derivatives, and the like. The therapeutic agent may also be other small organic molecules, naturally isolated entities or their analogs, organometallic agents, chelated metals or metal salts, peptide-based drugs, or peptidic or non-peptidic receptor targeting or binding agents. It is contemplated that linkage of the therapeutic agent to the matrix may be via a protease sensitive linker or other biodegradable linkage. Molecules which may be incorporated into the hydrogel matrix include, but are not limited to, vitamins and other nutritional supplements; glycoproteins (e.g., collagen); fibronectin; peptides and proteins; carbohydrates (both simple and/or complex); proteoglycans; antigens; oligonucleotides (sense and/or antisense DNA and/or RNA); antibodies (for example, to infectious agents, tumors, drugs or hormones); and gene therapy reagents.

In certain embodiments, one or more multifunctional cross-linking agents may be utilized as reactive moieties that covalently link biopolymers or synthetic polymers. Such bifunctional cross-linking agents may include glutaraldehyde, epoxides (e.g., bis-oxiranes), oxidized dextran, p-azidobenzoyl hydrazide, N-[α.-maleimidoacetoxy]succinimide ester, p-azidophenyl glyoxal monohydrate, bis-[β-(4-azidosalicylamido)ethyl]disulfide, bis[sulfosuccinimidyl]suberate, dithiobis[succinimidyl proprionate, disuccinimidyl suberate, 1-ethyl-3-[3-dimethylaminopropyl]carbodiimide hydrochloride (EDC), N-hydroxysuccinimide (NHS) and other bifunctional cross-linking reagents known to those skilled in the art. It should be appreciated by those in skilled in the art that the mechanical properties of the hydrogel are greatly influenced by the cross-linking time and the amount of cross-linking agents.

In another embodiment utilizing a cross-linking agent, polyacrylated materials, such as ethoxylated (20) trimethylpropane triacrylate, may be used as a non-specific photo-activated cross-linking agent. Components of an exemplary reaction mixture would include a thermoreversible hydrogel held at 39° C., polyacrylate monomers, such as ethoxylated (20) trimethylpropane triacrylate, a photo-initiator, such as eosin Y, catalytic agents, such as 1-vinyl-2-pyrrolidinone, and triethanolamine. Continuous exposure of this reactive mixture to long-wavelength light (>498 nm) would produce a cross-linked hydrogel network.

In one embodiment, the hydrogel comprises a UV sensitive curing agent which initiates hydrogel polymerization. For example, in one embodiment, a hydrogel comprises the photoinitiator 4-(2-hydroxyethoxy)phenyl-(2-hydroxy-2-propyl)ketone. In one embodiment, polymerization is induced by 4-(2-hydroxyethoxy)phenyl-(2-hydroxy-2-propyl)ketone upon application of UV light. Other examples of UV sensitive curing agents include 2-hydroxy-2-methyl-1-phenylpropan-2-one, 4-(2-hydroxyethoxy)phenyl (2-hydroxy-2-phenyl-2-hydroxy-2-propyl)ketone, 2,2-dimethoxy-2-phenyl-acetophenone 1-[4-(2-Hydroxyethoxy)-phenyl]-2 -hydroxy-2-methyl-1-propane-1-one, 1-hydroxycyclohexylphenyl ketone, trimethyl benzoyl diphenyl phosphine oxide and mixtures thereof.

The stabilized cross-linked hydrogel matrix of the present invention may be further stabilized and enhanced through the addition of one or more enhancing agents. By "enhancing agent" or "stabilizing agent" is intended any compound added to the hydrogel matrix, in addition to the high molecular weight components, that enhances the hydrogel matrix by providing further stability or functional advantages. Suitable enhancing agents, which are admixed with the high molecular weight components and dispersed within the hydrogel matrix, include many of the additives described earlier in connection with the thermoreversible matrix discussed above. The enhancing agent may include any compound, especially polar compounds, that, when incorporated into the cross-linked hydrogel matrix, enhance the hydrogel matrix by providing further stability or functional advantages.

Preferred enhancing agents for use with the stabilized cross-linked hydrogel matrix include polar amino acids, amino acid analogues, amino acid derivatives, intact collagen, and divalent cation chelators, such as ethylenediaminetetraacetic acid (EDTA) or salts thereof. Polar amino acids are intended to include tyrosine, cysteine, serine, threonine, asparagine, glutamine, aspartic acid, glutamic acid, arginine, lysine, and histidine. The preferred polar amino acids are L-cysteine, L-glutamic acid, L-lysine, and L-arginine. Suitable concentrations of each particular preferred enhancing agent are the same as noted above in connection with the thermoreversible hydrogel matrix. Polar amino acids, EDTA, and mixtures thereof, are preferred enhancing agents. The enhancing agents may be added to the matrix composition before or during the crosslinking of the high molecular weight components.

The enhancing agents are particularly important in the stabilized cross-linked bioactive hydrogel matrix because of the inherent properties they promote within the matrix. The hydrogel matrix exhibits an intrinsic bioactivity that will become more evident through the additional embodiments described hereinafter. It is believed the intrinsic bioactivity is a function of the unique stereochemistry of the cross-linked macromolecules in the presence of the enhancing and strengthening polar amino acids, as well as other enhancing agents.

In one embodiment, amniotic membrane powder or SAM is incorporated into the hydrogel. For example, amniotic membrane powder or SAM may be added to the hydrogel solution prior to gelation or polymerization of the gel. Amniotic membrane powder or SAM may be added to hydrogel solution in any amount desired to produce a desired effect. In one embodiment, the ratio of SAM to hydrogel solution ranges from about 10:1 to 1:10. In another embodiment, the ratio of SAM to hydrogel solution ranges from about 5:1 to 1:5. In another embodiment, the ratio of SAM to hydrogel solution is 1:1. In this way, components of amniotic membrane become interspersed within the hydrogel. In another embodiment, the polymerized hydrogel is coated with an effective amount of amniotic membrane powder or SAM. In some embodiments, the hydrogel permits diffusion of amniotic membrane components into and throughout the hydrogel.

(b) Electrospun Scaffolds

In one embodiment, the amniotic membrane powder or SAM of the present invention may be incorporated into nanofibrous biocompatible electrospun matrices. In some embodiments, the amniotic membrane powder or SAM is blended with a synthetic polymer, such as poly(ethylene oxide) (PEO) to produce a tissue engineering scaffold.

The scaffolds of the invention may be produced in a variety of ways. In an exemplary embodiment, the scaffold may be produced by electrospinning. Electrospinning is an atomization process of a conducting fluid which exploits the interactions between an electrostatic field and the conducting fluid. When an external electrostatic field is applied to a conducting fluid (e.g., a semi-dilute polymer solution or a polymer melt), a suspended conical droplet is formed, whereby the surface tension of the droplet is in equilibrium with the electric field. Electrostatic atomization occurs when the electrostatic field is strong enough to overcome the surface tension of the liquid. The liquid droplet then becomes unstable and a tiny jet is ejected from the surface of the droplet. As it reaches a grounded target, the material may be collected as an interconnected web containing relatively fine, i.e. small diameter, fibers. The resulting films (or membranes) from these small diameter fibers have very large surface area to volume ratios and small pore sizes. A detailed description of electrospinning apparatus is provided in Zong, et al., 2002 Polymer 43: 4403-4412; Rosen et al., 1990 Ann Plast Surg 25: 375-87; Kim, K., Biomaterials 2003, 24: 4977-85; Zong, X., 2005 Biomaterials 26: 5330-8. After electrospininng, extrusion and molding may be utilized to further fashion the polymers. To modulate fiber organization into aligned fibrous polymer scaffolds, the use of patterned electrodes, wire drum collectors, or post-processing methods such as uniaxial stretching has been successful. Zong, X., 2005 Biomaterials 26: 5330-8; Katta, P., 2004 Nano Lett 4: 2215-2218; Li, D., 2005 Nano Lett 5: 913-6.

The amniotic membrane comprising protein solution to be electrospun may be produced in one of several ways. One method involves adding the SAM solution to an appropriate solvent. This process may be accomplished in a syringe assembly or it may be subsequently loaded into a syringe assembly. Another method involves purchasing commercially available polymer solutions or commercially available polymers and dissolving them to create polymer solutions. For example, poly(ethylene oxide) (PEO) may be purchased from Sigma (Sigma, St. Louis, Mo.), poly-L-lactide (PLLA) may be purchased from DuPont (Wilmington, Del.), poly (lactide-co-glycolide) may be purchased from Ethicon (Somerville, N.J.). Additional polymer scaffold components of the invention, such as cells and biomolecules, are also commercially available from suppliers.

The protein solution comprising amniotic membrane used to form the scaffold is first dissolved in a solvent. The solvent may be any solvent which is capable of dissolving the amniotic membrane components. Typical solvents include a solvent selected from N,N-Dimethyl formamide (DMF), tetrahydrofuran (THF), methylene chloride, dioxane, ethanol, hexafluoroisopropanol (HFIP), chloroform, 1,1,1,3,3,3-hexafluoro-2-propanol (HFP), glacial acetic acid, water, and combinations thereof.

The protein solution may optionally contain a salt which creates an excess charge effect to facilitate the electrospinning process. Examples of suitable salts include NaCl, $KH_2PO_4$, $K_2HPO_4$, $KIO_3$, KCl, MgSO4, MgCl2, $NaHCO_3$, $CaCl_2$ or mixtures of these salts.

The protein solution forming the conducting fluid preferably has a protein concentration in the range of about 1 to about 80 wt %, more preferably about 8 to about 60 wt %.

The electric field created in the electrospinning process preferably is in the range of about 5 to about 100 kilovolts (kV), more preferably about 10 to about 50 kV. The feed rate of the conducting fluid to the spinneret (or electrode) preferably is in the range of about 0.1 to about 1000 microliters/min, more preferably about 1 to about 250 microliters/min.

The single or multiple spinnerets sit on a platform which is capable of being adjusted, varying the distance between the platform and the grounded collector substrate. The distance may be any distance which allows the solvent to essentially completely evaporate prior to the contact of the polymer with the grounded collector substrate. In an exemplary embodiment, this distance may vary from 1 cm to 25 cm. Increasing the distance between the grounded collector substrate and the platform generally produces thinner fibers.

In electrospinning cases where a rotating mandrel is required, the mandrel is mechanically attached to a motor, often through a drill chuck. In an exemplary embodiment, the motor rotates the mandrel at a speed of between about 1 revolution per minute (rpm) to about 500 rpm. In an exemplary embodiment, the motor rotation speed of between about 200 rpm to about 500 rpm. In another exemplary embodiment, the motor rotation speed of between about 1 rpm to about 100 rpm.

Additional embodiments or modifications to the electrospinning process and apparatus are described herein.

The invention also includes combinations of natural materials, combinations of synthetic materials, and combinations of both natural and synthetic materials. For example, the amniotic membrane powder or SAM of the invention may be combined with natural materials, synthetic materials, or both natural and synthetic materials to produce the scaffolds of the invention. Examples of combinations include, but are not limited to: blends of different types of collagen (e.g. Type I with Type II, Type I with Type III, Type II with Type III, etc.); blends of one or more types of collagen with fibrinogen, thrombin, elastin, PGA, PLA, and polydioxanone; and blends of fibrinogen with one or more types of collagen, thrombin, elastin, PGA, PLA, and polydioxanone.

The electroprocessed material of the present invention may result from the electroprocessing of natural materials, synthetic materials, or combinations thereof. Examples include but are not limited to amino acids, peptides, denatured peptides such as gelatin from denatured collagen, polypeptides, proteins, carbohydrates, lipids, nucleic acids, glycoproteins, lipoproteins, glycolipids, glycosaminoglycans, and proteoglycans.

Some preferred materials to be electroprocessed are naturally occurring extracellular matrix materials and blends of naturally occurring extracellular matrix materials, including but not limited to collagen, fibrin, fibrinogen, thrombin, elastin, laminin, fibronectin, hyaluronic acid, chondroitin 4-sulfate, chondroitin 6-sulfate, dermatan sulfate, heparin sulfate, heparin, and keratan sulfate, and proteoglycans. Especially preferred materials for electroprocessing include collagen, fibrin, fibrinogen, thrombin, fibronectin, and combinations thereof. Some collagens that are used include but are not limited to collagen types I, II, III, IV, V, VI, VII, VIII, IX, X, XI, XII, XIII, XIV, XV, XVI, XVII, XVIII, and XIX. Some preferred collagens include types I, II, and III. These proteins may be in any form, including but not limited to native and denatured forms. Other preferred materials for electroprocessing are carbohydrates such as polysaccharides (e.g. cellulose and its derivatives), chitin, chitosan, alginic acids, and alginates such as calcium alginate and sodium alginate. These materials may be isolated from plant products, humans or other organisms or cells or synthetically manufactured. Some especially preferred natural materials for electroprocessing are collagen, fibrinogen, thrombin, fibrin, fibronectin, and combinations thereof. Also included are crude extracts of tissue, extracellular matrix material, extracts of non-natural tissue, or extracellular matrix materials (i.e. extracts of cancerous tissue), alone or in combination. Extracts of biological materials, including but are not limited to cells, tissues, organs, and tumors may also be electroprocessed.

Collagen and fibrinogen may each been electrospun to produce fibers having repeating, band patterns along the length of the fibers. These patterns are observable, for example with transmission electron microscopy, and are typical of those produced by natural processes. In some embodiments, the banded pattern observed in electrospun collagen fibers is the same as that produced by cells in vivo. In some embodiments, the banding pattern in electrospun fibrinogen is the same as that of fibrinogen found in normal clots formed in vivo. While not wishing to be bound by any particular theory, it is believed that the banding apparent along natural collagen fibers results from the helical pattern of the protein chains in the collagen, while the banding in fibrinogen in vivo results from close packing of individual fibrin molecules in a stacked configuration. In some of these embodiments, the compositions are composed of fibrous webs rather than networks characteristic of fibrin clots. Further, in some embodiments, electroprocessed fibrinogen is not soluble in water, unlike native fibrinogen.

The invention includes all natural or natural-synthetic hybrid compositions that result from the electroprocessing of any material. Materials that change in composition or structure before, during, or after electroprocessing are within the scope of the invention.

It is to be understood that these electroprocessed materials may be combined with other materials and/or substances in forming the compositions of the present invention. For example, in some embodiments an electroprocessed peptide is combined with an adjuvant to enhance immunogenicity when implanted subcutaneously. Electroprocessed materials in some embodiments are prepared at very basic or acidic pHs (for example, by electroprocessing from a solution having a specific pH) to accomplish the same effect. As another example, an electroprocessed matrix, containing cells, may be combined with an electroprocessed biologically compatible polymer to stimulate growth and division of the cells in the electroprocessed matrix.

Synthetic materials electroprocessed for use in the scaffold include any materials prepared through any method of artificial synthesis, processing, isolation, or manufacture. The synthetic materials are preferably biologically compatible for administration in vivo or in vitro. Such polymers include but are not limited to the following: poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactic acid (PLA), polyglycolic acids (PGA), poly(lactide-co-glycolides) (PLGA), nylons, polyamides, polyanhydrides, poly(ethylene-co-vinyl alcohol) (EVOH), polycaprolactone, poly(vinyl acetate) (PVA), polyvinylhydroxide, poly(ethylene oxide) (PEO) and polyorthoesters or any other similar synthetic polymers that may be developed that are biologically compatible. Some preferred synthetic materials include PLA, PGA, copolymers of PLA and PGA, polycaprolactone, poly(ethylene-co-vinyl acetate), EVOH, PVA, and PEO. Polymers with cationic moieties are also preferred in some embodiments. Examples of such polymers include, but are not limited to, poly(allyl amine), poly (ethylene imine), poly(lysine), and poly(arginine). The polymers may have any molecular structure including, but not limited to, linear, branched, graft, block, star, comb and dendrimer structures. Matrices may be formed of electrospun fibers, electroaerosol, electrosprayed, or electrosputtered droplets, electroprocessed powders or particles, or a combination of the foregoing.

By selecting different natural and synthetic materials, or combinations thereof, many characteristics of the scaffold are manipulated. The properties of the matrix comprised of electroprocessed material and a substance may be adjusted. In addition, selection of materials for electroprocessing may affect the permanency of an implanted matrix. For example, many matrices made by electroprocessing fibrinogen or fibrin may degrade more rapidly while many matrices made of collagen are more durable and many other matrices made by electroprocessing materials are more durable still. Thus, for example, incorporation of durable synthetic polymers (e.g. PLA, PGA) increase the durability and structural strength of matrices electroprocessed from solutions of fibrinogen in some embodiments. Use of matrices made by electroprocessing natural materials such as proteins derived from corn, wheat, potato, sorghums, tapioca, rice, arrow root, sago, soybean, pea, sunflower, peanut, gelatin, and the like also minimize rejection or immunological response to an implanted matrix. Accordingly, selection of materials for electroprocessing and use in substance delivery is influenced by the desired use.

In embodiments in which the matrix contains substances that are to be released from the matrix, incorporating electroprocessed synthetic components, such as biocompatible substances, can modulate the release of substances from an electroprocessed composition. For example, layered or laminate structures may be used to control the substance release profile. Unlayered structures may also be used, in which case the release is controlled by the relative stability of each component of the construct. For example, layered structures composed of alternating electroprocessed materials are prepared by sequentially electroprocessing different materials onto a target. The outer layers are, for example, tailored to dissolve faster or slower than the inner layers. Multiple agents may be delivered by this method, optionally at different release rates. Layers may be tailored to provide a complex, multi-kinetic release profile of a single agent over time. Using combinations of the foregoing provides for release of multiple substances released, each with its own profile. Complex profiles are possible.

Natural components such as biocompatible substances may be used to modulate the release of electroprocessed materials or of substances from an electroprocessed composition. For example, a drug or series of drugs or other materials or substances to be released in a controlled fashion may be electroprocessed into a series of layers. In one embodiment, one layer is composed of electroprocessed fibrinogen plus a drug, the next layer PLA plus a drug, a third layer is composed of polycaprolactone plus a drug. The layered construct may be implanted, and as the successive layers dissolve or break down, the drug (or drugs) is released in turn as each successive layer erodes. In some embodiments, unlayered structures are used, and release is controlled by the relative stability of each component of the construct.

In some embodiments, the electroprocessed material itself may provide a therapeutic effect. Non-limiting examples of a material that has a therapeutic effect is electroprocessed fibrinogen, thrombin, fibrin, or combinations thereof. For example, thrombin converts fibrinogen to fibrin. Fibrin assists in arrest of bleeding (hemostasis). Fibrin is a component of the provisional matrix that is laid down during the early stages of healing and may also promote the growth of vasculature in adjacent region. In many ways fibrin is a natural healing promoter. In some embodiments, electroprocessed fibrinogen also assists in healing. When placed in contact with a wound of a patient, such an electroprocessed material provides the same healing properties as fibrin.

(c) Method for Forming Matrices or Scaffolds

A biocompatible scaffold may be shaped using methods such as, for example, solvent casting, compression molding, filament drawing, meshing, leaching, weaving, foaming, electrospinning and coating. In solvent casting, a solution of one or more proteins in an appropriate solvent, is cast as a branching pattern relief structure. After solvent evaporation, a thin film is obtained. In compression molding, a polymer is pressed at pressures up to 30,000 pounds per square inch into an appropriate pattern. Filament drawing involves drawing from the molten polymer and meshing involves forming a mesh by compressing fibers into a felt-like material. In leaching, a solution containing two materials is spread into a shape close to the final form of the artificial organ. Next a solvent is used to dissolve away one of the components, resulting in pore formation. (See U.S. Pat. No. 5,514,378 to Mikos).

The scaffold may be shaped into any number of desirable configurations to satisfy any number of overall system, geometry or space restrictions. For example, in the use of the scaffold for bladder, urethra, valve, or blood vessel reconstruction, the matrix or scaffold may be shaped to conform to the dimensions and shapes of the whole or a part of the tissue. The scaffold may be shaped in different sizes and shapes to conform to the organs of differently sized patients. For bladders, the scaffold should be shaped such that after its biodegradation, the resulting reconstructed bladder may be collapsible when empty in a fashion similar to a natural bladder. The matrix or scaffold may also be shaped in other fashions to accommodate the special needs of the patient.

In one embodiment, the scaffolds are seeded with one or more populations of cells to form an artificial organ construct. The artificial organ construct may be autologous, where the cell populations are derived from the subject's own tissue, or allogenic, where the cell populations are derived from another subject within the same species as the patient. The artificial organ construct may also be xenogenic, where the different cell populations are derived form a mammalian species that is different from the subject. For example the cells may be derived from organs of mammals such as humans, monkeys, dogs, cats, mice, rats, cows, horses, pigs, goats and sheep.

Cells may be isolated from a number of sources, including, for example, biopsies from living subjects and whole-organ recover from cadavers. The isolated cells are preferably autologous cells, obtained by biopsy from the subject intended to be the recipient. For example, a biopsy of skeletal muscle from the arm, forearm, or lower extremities, or smooth muscle from the area treated with local anesthetic with a small amount of lidocaine injected subcutaneously, and expanded in culture. The biopsy may be obtained using a biopsy needle, a rapid action needle which makes the procedure quick and simple.

Cells may be isolated using techniques known to those skilled in the art. For example, the tissue or organ may be disaggregated mechanically and/or treated with digestive enzymes and/or chelating agents that weaken the connections between neighboring cells making it possible to disperse the tissue into a suspension of individual cells without appreciable cell breakage. Enzymatic dissociation may be accomplished by mincing the tissue and treating the minced tissue with any of a number of digestive enzymes either alone or in combination. These include but are not limited to trypsin, chymotrypsin, collagenase, elastase, and/or hyaluronidase, DNase, pronase and dispase. Mechanical disruption may also be accomplished by a number of methods including, but not limited to, scraping the surface of the organ, the use of grinders, blenders, sieves, homogenizers, pressure cells, or in sonicators.

Preferred cell types include, but are not limited to, urothelial cells, mesenchymal cells, especially smooth or skeletal muscle cells, myocytes (muscle stem cells), fibroblasts, chondrocytes, adipocytes, fibromyoblasts, and ectodermal cells, including ductile and skin cells, hepotocytes, Islet cells, cells present in the intestine, and other parenchymal cells, osteoblasts and other cells forming bone or cartilage. In some cases, it may also be desirable to include nerve cells. In other cases, it may be desirable to include stem cells.

Once the tissue has been reduced to a suspension of individual cells, the suspension may be fractionated into subpopulations from which the cells elements may be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counterstreaming centrifugation), unit gravity separation, countercurrent distribution, electrophoresis and fluorescence-activated cell sorting.

Cell fractionation may also be desirable, for example, when the donor has diseases such as cancer or metastasis of other tumors to the desired tissue. A cell population may be sorted to separate malignant cells or other tumor cells from normal noncancerous cells. The normal noncancerous cells, isolated from one or more sorting techniques, may then be used for organ reconstruction.

Isolated cells may be cultured in vitro to increase the number of cells available for coating the biocompatible scaffold. The use of allogenic cells, and more preferably autologous cells, is preferred to prevent tissue rejection. However, if an immunological response does occur in the subject after implantation of the artificial organ, the subject may be treated with immunosuppressive agents such as, cyclosporin or FK506, to reduce the likelihood of rejection.

In certain embodiments, chimeric cells, or cells from a transgenic animal, may be coated onto the biocompatible scaffold.

Isolated cells may be transfected prior to coating with genetic material. Useful genetic material may be, for example, genetic sequences which are capable of reducing or eliminating an immune response in the host. For example, the expression of cell surface antigens such as class I and class II histocompatibility antigens may be suppressed. This may allow the transplanted cells to have reduced chance of rejection by the host. In addition, transfection could also be used for gene delivery.

Isolated cells may be normal or genetically engineered to provide additional or normal function. Methods for genetically engineering cells with retroviral vectors, polyethylene glycol, or other methods known to those skilled in the art may be used. These include using expression vectors which transport and express nucleic acid molecules in the cells. (See Goeddel; Gene Expression Technology: Methods in Enzymology 185, Academic Press, San Diego, Calif. (1990).

Vector DNA is introduced into prokaryotic or cells via conventional transformation or transfection techniques. Suitable methods for transforming or transfecting host cells can be found in Sambrook et al. (Molecular Cloning: A Laboratory Manual, 3nd Edition, Cold Spring Harbor Laboratory press (2001)), and other laboratory textbooks.

Seeding of cells onto the matrix or scaffold may be performed according to standard methods. For example, the seeding of cells onto polymeric substrates for use in tissue repair has been reported (see, e.g., Atala, A. et al., J. Urol. 148(2 Pt 2): 658-62 (1992); Atala, A., et al. J. Urol. 150 (2 Pt 2): 608-12 (1993)). Cells grown in culture may be trypsinized to separate the cells, and the separated cells may be seeded on the matrix. Alternatively, cells obtained from cell culture may be lifted from a culture plate as a cell layer, and the cell layer may be directly seeded onto the scaffold without prior separation of the cells.

In a preferred embodiment, in the range of 1 million to 700 50 million cells are suspended in medium and applied to each square centimeter of a surface of a scaffold. Preferably, between 1 million and 50 million cells, and more preferably, between 1 million and 10 million cells are suspended in media and applied to each square centimeter of a surface of a scaffold. The matrix or scaffold is incubated under standard culturing conditions, such as, for example, 37° C., 5% $CO_2$, for a period of time until the cells attached. However, it will be appreciated that the density of cells seeded onto the scaffold may be varied. For example, greater cell densities promote greater tissue regeneration by the seeded cells, while lesser densities may permit relatively greater regeneration of tissue by cells infiltrating the graft from the host. Other seeding techniques may also be used depending on the matrix or scaffold and the cells. For example, the cells may be applied to the matrix or scaffold by vacuum filtration. Selection of cell types, and seeding of cells onto a scaffold, will be routine to one of ordinary skill in the art in light of the teachings herein.

In one embodiment, the scaffold is seeded with one population of cells to form an artificial organ construct. In another embodiment, the matrix or scaffold is seeded on two sides with two different populations of cells. This may be performed by first seeding one side of the matrix or scaffold and then seeding the other side. For example, the scaffold may be placed with one side on top and seeded. Then the matrix or scaffold may be repositioned so that a second side is on top. The second side may then be seeded with a second population of cells. Alternatively, both sides of the matrix or scaffold may be seeded at the same time. For example, two cell chambers may be positioned on both sides (i.e., a sandwich) of the scaffold. The two chambers may be filled with different cell populations to seed both sides of the matrix or scaffold simultaneously. The sandwiched scaffold may be rotated, or flipped frequently to allow equal attachment opportunity for both cell populations. Simultaneous seeding may be preferred when the pores of the matrix or scaffold are sufficiently large for cell passage from one side to the other side. Seeding the scaffold on both sides simultaneously may reduce the likelihood that the cells would migrate to the opposite side.

In another embodiment, two separate scaffolds may be seeded with different cell populations. After seeding, the two matrices may be attached together to form a single matrix or scaffold with two different cell populations on the two sides. Attachment of the scaffolds to each other may be performed using standard procedures such as fibrin glue, liquid copolymers, sutures and the like.

In order to facilitate cell growth on the scaffold of the present invention, the scaffold may be coated with one or more cell adhesion-enhancing agents. These agents include but are not limited collagen, laminin, and fibronectin. The scaffold may also contain cells cultured on the scaffold to form a target tissue substitute. The target tissue that may be formed using the scaffold of the present invention may be an arterial blood vessel, wherein an array of microfibers is arranged to mimic the configuration of elastin in the medial layer of an arterial blood vessel. In the alternative, other cells may be cultured on the scaffold of the present invention. These cells include, but are not limited to, cells cultured on the scaffold to form a blood vessel substitute, epithelial cells cultured on the scaffold to form epithelial tissue, muscle cells cultured on the scaffold to form muscle tissue, endothelial cells cultured on the scaffold to form endothelial tissue, skeletal muscle cells cultured on the scaffold to form skeletal muscle tissue, cardiac muscle cells cultured on the scaffold to form cardiac muscle tissue, collagen fibers cultured on the scaffold to form cartilage, interstitial valvular cells cultured on the scaffold to form valvular tissue and mixtures thereof.

Therapeutics

The in vivo studies presented herein demonstrate incorporation of SAM into a bioprintable, UV crosslinked hydrogel. By way of a non-limiting example, SAM was incorporated within a hyaluronic acid (HA)-based hydrogel that, in certain instances is bioprinted over wounds and photocrosslinked in place. Accordingly, the present invention provides methods to promote wound healing and tissue regeneration. In one embodiment, the method comprises administering the amniotic membrane-containing composition of the invention to a wound or treatment site of a subject.

In one embodiment, the photocrosslinking step may be performed under electromagnetic radiation, e.g., in the visible, ultraviolet (UV), near infrared, infrared, and/or microwave regions. The photocrosslinking may also be performed using gamma rays, X-rays, or radio waves as appropriate.

In some embodiments, the photocrosslinking is performed in the presence of a photoinitiator. The photocrosslinking may also be performed using a crosslinker, e.g., a UV crosslinker.

In some embodiments, the method of the invention is used to crosslink SAM together with a hyaluronic acid (HA)-based hydrogel, thereby forming a SAM hydrogel. The hydrogel may have a structure, e.g., including one or more of a micro thin film, a micro pad, a micro thin fiber, a nanosphere or a microsphere. In some embodiments, the structures are fabricated by emulsification, photolithography, microfluidic synthesis, micromolding, or micro-electrospinning, or a combination thereof. The method may also be used to coat the hydrogel on the surface of a substrate.

In some embodiments, photocrosslinking is carried out by exposing the SAM with a hydrogel to an appropriate source of electromagnetic radiation e.g., a source of ultraviolet (UV) or visible light, near infrared, infrared wavelengths and microwaves. In some embodiments, gamma rays, X-rays, radio waves are used. A variety of bulbs, lasers or fibers may be used to provide illumination. In some embodiments, light emitting diodes (LEDs) are used. Different wavelengths are possible. In some embodiments, different illumination sources are used to form one hydrogel matrix. Any such combination of photoreactive groups and light sources useful for creating the amniotic membrane-based hydrogels of the present invention are within the scope of the invention.

The cross-linked hydrogel composition of the invention may be cross-linked outside the body and then implanted into a patient, or the hydrogel may be allowed to cross-link in situ.

In one application, the invention provides a method of promoting the closure of a wound in a patient using the composition of the invention. In one embodiment, the method of the invention is useful for clinical and personal wound care and soft tissue regeneration. In accordance with the method, the amniotic membrane-containing composition is transferred to the vicinity of a wound. The method promotes closure of both external (e.g., surface) and internal wounds. Wounds for which the present inventive method is useful in promoting closure include, but are not limited to, abrasions, avulsions, blowing wounds, burn wounds, contusions, gunshot wounds, incised wounds, open wounds, penetrating wounds, perforating wounds, puncture wounds, seton wounds, stab wounds, surgical wounds, subcutaneous wounds, or tangential wounds. The method need not achieve complete healing or closure of the wound; it is sufficient that the method serve to promote any degree of wound closure. In this respect, the method may be employed alone or as an adjunct to other methods for healing wounded tissue.

In one embodiment, the composition comprising amniotic membrane powder or SAM is applied directly to a wound or treatment site of a subject. As described elsewhere herein, the amniotic membrane powder or SAM may be incorporated into a pharmaceutical formulation including topical ointments, creams, aerosol sprays, and the like.

In one aspect of the invention, the method comprises using an amniotic membrane-based scaffold, described elsewhere herein, as a wound dressing or graft for external skin wounds. In a clinical setting, the scaffold may be used to treat wounds resulting from trauma, burns, ulcers, abrasions, lacerations, surgery, or other damage. Surgeons can use these scaffolds to cover and protect the wound area, to temporarily replace lost or damaged skin tissue, and to guide new tissue generation and wound healing into the damaged area. In a clinical setting, in some embodiments, the scaffold may be secured to the wound area using sutures, adhesives, or overlaying bandages. The scaffold may be cut to match the size of the wound, or may overlap the wound edges. In some instances the scaffold may be shaped to penetrate into cavities formed by deep wounds.

In one embodiment, an amniotic membrane-based scaffold is applied in a flowable state to a wound or treatment site. In some instances, the scaffold polymerizes at the wound or treatment site. In one embodiment, the scaffold is induced to polymerize, for example through the application of UV light. For example, in one embodiment, an amniotic membrane-based hydrogel is applied to a wound or treatment site while the hydrogel is in a flowable state. The flowable hydrogel may be administered by any method known in the art. In one embodiment, the hydrogel is administered through a syringe. In another embodiment, the hydrogel is bioprinted at the wound or treatment site.

Bioprinting has emerged as a flexible tool with potential in a variety of tissue engineering and regenerative medicine applications. Bioprinting may be described as robotic deposition that has the potential to build organs or tissues (Visconti et al., 2010, Expert Opin Biol Ther, 10: 409-420). In general, bioprinting uses a computer controlled printing device to accurately deposit cells and biomaterials into precise three-dimensional (3-D) geometries in order to create anatomically correct structures. These devices have the ability to print cells (the "bio-ink") in the form of cell aggregates, cells encapsulated in hydrogels, or cell-seeded microcarriers. The polymers that provide structure or space-holding capabilities are serving as the "bio-paper" (Fedorovich et al., 2007, Tissue Eng, 13: 1905-1925; Mironov et al., 2003, Trends Biotechnol, 21: 157-161).

In some instances, application of a flowable composition is beneficial as it can fill irregular shaped wounds and penetrate through deep wounds not accessible by solid grafts or patches. In some instances, the hydrogel comprises a photoinitiator or UV sensitive curing agent that allows nearly instantaneous polymerization of the hydrogel upon administration of light at the appropriate wavelength.

In another aspect of the invention, the method comprises using amniotic membrane-containing compositions for personal and home care. In one embodiment, the composition is applied to bandage. In another embodiment, an amniotic membrane-based scaffold is combined with an adhesive backing to create a bandage. An adhesive section may hold the scaffold in place on a wounded area and may be removed when the scaffold degrades or fuse with the tissue. The scaffold may also be secured with a liquid or gel adhesive.

In another aspect of the invention, scaffolds may be used as gauze to absorb fluid and protect large wounds. This scaffold gauze may be wrapped around a wounded area or secured with tape.

In another aspect, the method of the invention may be used to treat internal soft tissue wounds such as wounds in the amniotic sac, ulcers in the gastrointestinal tract or mucous membranes, gingival damage or recession, internal surgical incisions or biopsies, etc. In one embodiment, the method comprises suturing or adhering an amniotic membrane-based scaffold to fill or cover the damaged tissue area.

The scaffold has numerous characteristics that are useful for wound healing. First, the polymer biomaterials described herein that include nanofibers are both nano-porous and breathable. They can prevent microbes and infectious particles from crossing through, but they allow air flow and moisture penetration which are critical in natural wound healing.

In some instances, the fibers in this invention are biodegradable, which allows for temporary wound coverage followed by eventual ingrowth of new tissue. The choice of material for wound dressings can be determined to match the natural tissue characteristics including mechanical strength and rate of degradation/tissue regeneration.

In some instances, the biomaterials may be embedded or conjugated with various factors which may be released upon degradation. These factors may include, but are not limited to epidermal growth factor (EGF), platelet derived growth factor (PDGF), basic fibroblast growth factor (bFGF), transforming growth factor-.beta. (TGF-0), and tissue inhibitors of metalloproteinases (TIMP), which have been shown to be beneficial in wound healing. Additional wound healing factors such as antibiotics, bacteriocides, fungicides, silver-containing agents, analgesics, and nitric oxide releasing compounds may also be incorporated into the scaffold wound dressings or grafts.

In some instances, scaffolds for wound healing may be seeded with cells for faster tissue regeneration and more natural tissue structure. These cells may include, but are not limited to fibroblasts, keratinocytes, epithelial cells, endothelial cells, mesenchymal stem cells, and/or stem cells.

In some instances, the nano-scale architecture of the scaffolds closely mimics that of the extracellular matrix (ECM) of many common soft tissues. For example, the nano-scale fibers are structurally similar to collagen fibrils found in skin and other tissues. This architecture may prevent scar formation by providing an organized scaffold for cells to migrate into a wound. In this aspect of the invention, alignment of the scaffold is preferred to keep cells aligned and organized, rather than allowing them to arrange randomly as in the formation of scar tissue. Aligned biomaterial scaffolds may be oriented with respect to a given axis of the wound to allow faster tissue ingrowth and wound coverage.

Scaffold alignment may also be used to closely match the architecture of natural tissue ECM. This may include fiber alignment in a single direction, criss-cross alignment in orthogonal directions, or more complicated fiber architecture. In this instance of the invention, the scaffold includes multiple layers of fibers with specific fiber orientation in each layer. Similarly, each individual scaffold layer may also contain a specific factor or cell type such as the ones listed previously. This allows for creation of polymer scaffolds that can closely match natural tissue architecture and composition. For example, a simple scaffold wound dressing or graft might include a single layer of aligned fibers. On the other hand, a more complex scaffold skin graft might include multiple aligned fiber sheets layered in a criss-cross pattern with fibroblasts in the bottom sheets and keratinocytes in the top sheet, as well as bFGF in the bottom sheets and an antimicrobial agent in the top sheet. Other such combinations are possible, depending on the specific needs of the patient.

The invention also encompasses tissue regeneration applications. The objective of the tissue regeneration therapy approach is to deliver high densities of repair-competent cells (or cells that can become competent when influenced by the local environment) to the defect site in a format that optimizes both initial wound mechanics and eventual neotissue production The composition of the invention may be administered to an individual in need thereof in a wide variety of ways. Preferred modes of administration include intravenous, intravascular, intramuscular, subcutaneous, intracerebral, intraperitoneal, soft tissue injection, surgical placement, arthroscopic placement, and percutaneous insertion, e.g. direct injection, cannulation or catheterization. Most preferred methods result in localized administration of the inventive composition to the site or sites of tissue defect. Any administration may be a single application of a composition of invention or multiple applications. Administrations may be to single site or to more than one site in the individual to be treated. Multiple administrations may occur essentially at the same time or separated in time.

In one embodiment, the present invention provides the use of amniotic membrane-containing compositions in tissue engineering. In this regard, the invention provides a method of producing animal matter comprising administering an amniotic membrane containing composition to induce the formation or regeneration of the desired matter. The matter may include mature tissues, or even whole organs, including tissue types into which the inventive cells can differentiate (as set forth herein). Typically, such matter will comprise adipose, cartilage, heart, dermal connective tissue, blood tissue, nervous tissue, muscle, kidney, bone, pleural, splanchnic tissues, vascular tissues, and the like. More typically, the matter will comprise combinations of these tissue types (i.e., more than one tissue type). For example, the matter may comprise all or a portion of an animal organ (e.g., a heart, a kidney) or a limb (e.g., a leg, a wing, an arm, a hand, a foot, etc.). Of course, in as much as the cells can divide and differentiate to produce such structures, they can also form anlagen of such structures. At early stages, such anlagen can be cryopreserved for future generation of the desired mature structure or organ.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art may, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Solubilized Amniotic Membrane (SAM) Containing Hydrogel

Experiments were designed to create a wound healing product with high clinical efficiency, and preferably one that does not require a cellular component, yet retains the bioactivity of a cellular treatment.

Amniotic membrane patches have been implemented as dressings for skin wounds for many years. However, application of freeze-dried or cryopreserved patches (amnion-based or artificial grafts as described above) is not optimal for the many wounds that are irregularly-shaped and/or variable depth. To address this problem, a protocol for solubilizing amniotic membrane samples to produce a solubilized amniotic membrane (SAM) solution which can be combined with a number of materials for deposition over wounds was developed. SAM is a cell-free solution, containing cytokines, extracellular matrix (ECM) ECM-associated proteins and other factors that are known to promote wound healing and modulate inflammatory responses. The key difference between SAM and other products is that SAM is derived from amnion membrane that is complete with all cells and ECM present, so contains many factors that would be lost following decellularization. Further, the use of a ECM rich solution has advantages over products in the form of sheets/patches of amnion membrane in the ability to fill irregular and deep wounds. This solution may be utilized in many formats including as a liquid or aerosol directly applied to a wound, used to soak bandages/scaffolds prior to placement or incorporated into gels or other solutions (antibiotic/analgesics).

The in vivo studies were designed to incorporate SAM into a bioprintable, UV crosslinked hydrogel. Specifically, SAM was implemented together with a hyaluronic acid (HA)-based hydrogel that may be bioprinted over wounds and photocrosslinked in place nearly instantaneously. The results presented herein demonstrate the effectiveness of using HA-SAM to treat wounds in a murine wound healing model.

The materials and methods employed in these experiments are now described.

Preparation of Solubilized Amniotic Membrane

Solubilized amniotic membrane (SAM) was generated from amnions harvested from term human pregnancy tissue. Donated human placenta was collected and stored at 4° C. until further use. The amnion membrane (avascular/inner) was manually dissected from the chorion membrane (vascular/outer). Any blood clots which were present were removed. The membrane was washed with 500-1000 mL of sterile saline.

Using sterile scissors and forceps, the amnion membrane was cut into approximately 5×5 cm pieces. The amnion pieces were then transferred into a sterile 500 mL container and washed five times with 100 mL sterile saline. Pieces were then washed with 500 mL sterile water.

The amnion pieces were transferred into 50 mL tubes. During transfer, the pieces were dragged along the edge of the 500 mL container in order to remove as much water as possible from each piece. Each 50 mL tube was filled to a maximum of 25 mL. The 50 mL tubes containing the amnion pieces were then kept at −80° C. for 12-24 hours.

The lids of the 50 mL tubes were removed, and the tubes were covered with parafilm. Several small holes were poked into the parafilm. The tubes were placed in a pre-cooled glass lyophilizer container, and were lyophilized for 48-72 hours.

A SPEX SamplePrep 8970 freezer/mill was filled with liquid nitrogen. The lyophilized amnion membrane pieces were placed into the freezer/mill chamber. Membrane pieces were milled for 3 cycles of 5 minutes of cool, 5 minutes of mill. Following the grinding, 220 mg of amnion powder and 22 mg of pepsin was added into a 15 mL tube. The tube was then gamma irradiated for 1 hour at 1 mega rad. Following gamma radiation, all subsequent steps were performed in sterile conditions. Ten milliliters of sterilized 0.01N HCl was added to the tube. The materials within the tube were then mixed, allowing to digest for 48 hours at 37° C.

The digest was centrifuged at 4500 RPM for 10 minutes. The supernatant was removed and placed in another 15 mL tube. The solution was neutralized with NaOH to a pH of 7. The solution was stored in aliquots at −80° C. until further use.

Preparation of Amniotic Powder

For treatments using amniotic powder, the powder was generated as described above in the preparation of SAM. However, following gamma irradiation, pepsin was not added and no further processing steps were taken. The powder was stored in aliquots at −80° C. until further use.

Preparation of Hydrogel

Figure 1B:
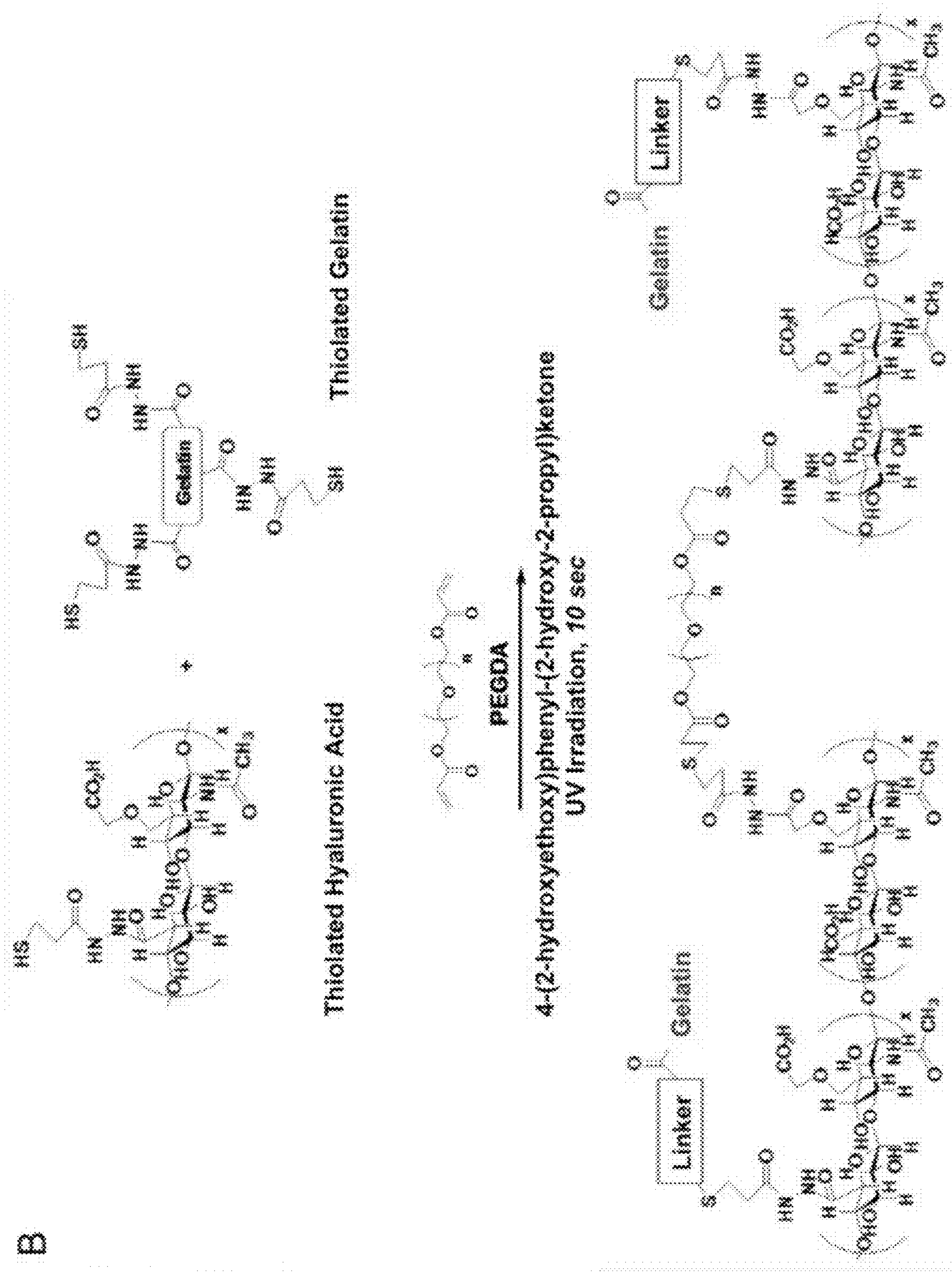

FIG. 1B provides a diagram demonstrating the chemistry by which the hydrogel of the invention is formed using thiol-ene photopolymerization chemistry. Briefly, hyaluronic acid (HA) and gelatin are thiolated, and then crosslinked with PEGDA in the presence of the photoinitiator 4-(2-hydroxyethoxy)phenyl-(2-hydroxy-2-propyl)ketone using irradiation with UV light. SAM solution was incorporated into the HA hydrogel solution at a 1:1 ratio prior UV cross-linking. For bioprinting, solutions were prepared as described above in tubes and loaded into the printer. In the case of photocrosslinkable hydrogels, all components were mixed together in one tube. The device consists of a carriage with 3-axis movement capability in which is housed the main print head. The print head is made up of a set of pressure-driven nozzles through which the hydrogel solutions are printed, and an additional set of high-pressure nozzles for secondary solutions, if required, such as crosslinkers to be printed. The hydrogel solutions are housed in swappable cartridges in line with the back pressure and the print heads. The printing process is controlled using a software platform that uses a scanner to measure wound size and depth, and controls nozzle position and solution flow to print optimal volumes of solution within the wound site.

In Vitro Assays

Keratinocyte and fibroblast viability was determined after encapsulation in the HA-SAM and exposing to UV light for 30 s to initiate crosslinking. A LIVE/DEAD assay was used to measure ratio of living/dead cells. A MTS assay was used to measure the effect of SAM on keratinocyte and fibroblast proliferation in vitro. A proteomics array was performed to measure levels of cytokines involved in cell proliferation, migration and neovascularization.

Skin Wound Model

Wounds, 2.0×2.0 cm full thickness, were created on the dorsal skin of nude mice. HA-SAM or HA-only gels were deposited and crosslinked within the wounds. Control mice received no treatment other than standard bandaging procedures. Wound size, re-epithelialization, and contraction were measured immediately after surgery, and at day 4, 7, 10, and 14, after which the animals were euthanized and the regenerated skin was harvested for histological analysis.

In the porcine model, full thickness 4.0×4.0 cm full thickness wounds were created on the dorsal flanks of Specific Pathogen Free (SPF) Yorkshire pigs. HA-SAM gels were deposited and crosslinked within the wounds. Additionally, sterilized amnion powder, was applied to the wounds, either directly as a powder, or following resuspension in saline solution. Control wounds received other commercially available wound healing products GraftJacket® or Amniograft®, as well as experimental electrospun wound healing scaffolds. Additional control wounds received no treatment other than standard bandaging procedures. Wound size, re-epithelialization, and contraction were measured immediately after surgery, and at day 4, 7, 10, 14, 18, 21, 24, and 28 after which the animals were euthanized and the regenerated skin was harvested for histological and biochemical analysis.

Skin Thickness

Examination of skin thickness was performed on hematoxylin and eosin-stained histological sections, using imaging software to measure the thickness of both the epidermis and dermis components of the regenerated tissues.

In Vivo Cell Proliferation

In vivo cell proliferation was measured by performing immunohistochemical staining for the proliferation marker Ki-67, together with a marker of the epidermis, Keratin 10. Ki-67 antibodies labeled proliferating cells, and Keratin 10 antibodies provided localization information for the epidermis.

Hydrogel Swelling

Hydrogel swelling experiments were performed by adding 3 mL of saline to 0.5 mL crosslinked hydrogels, and measuring weight of the hydrogels every 6 hours for a period of 24 hours. During each weighing, surface buffer was carefully removed in order to only weigh the swollen hydrogel network. The vials in which the gels were contained were weighed before the experiment, and vial weights were subtracted from later vial-gel weights to give gel-only weights for analysis.

Protein Release

Protein release was measured by adding 0.1 mL of saline to 0.1 mL aliquots of crosslinked hydrogels, incubating for 24 hours and removing the saline for analysis. Total protein concentration in the saline solution was measured by with a colorimetric assay and a protein standard curve. Following measurement, the volume of removed saline was replaced with fresh saline and the process repeated. This was continued for a period of 14 days.

The results of the experiments are now described.

Amniotic Membrane Compositions for Wound Healing

Figure 2A:
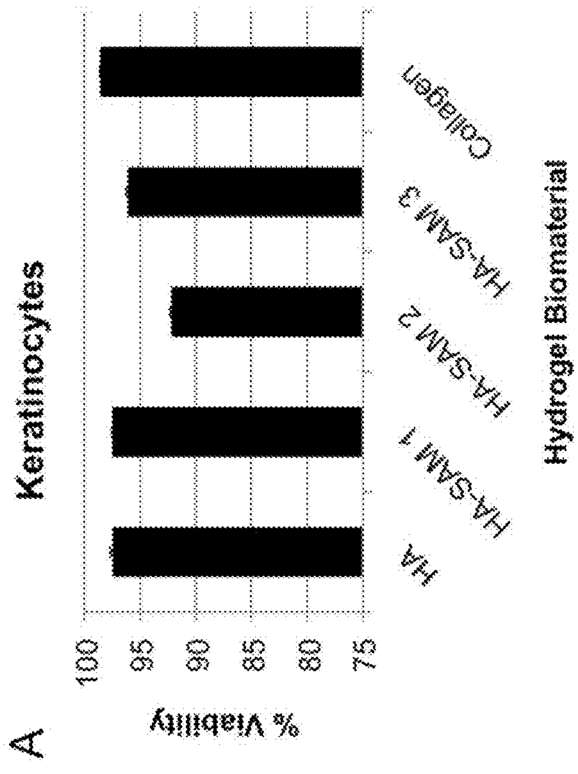
FIGS. 2A-2B depict the results of experiments.
Figure 2B:
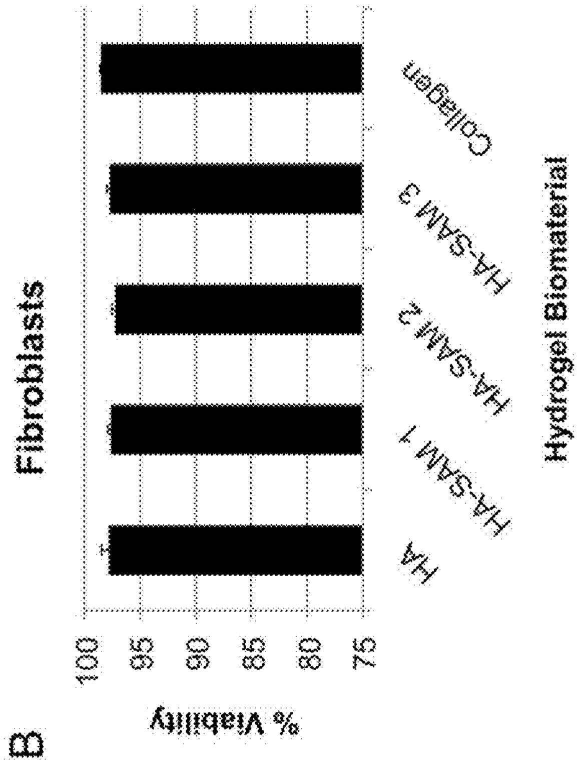

In the experiments presented herein HA-SAM hydrogels and HA gel+amnion are used interchangeably. Primary keratinocytes and fibroblasts were evaluated for their ability to survive within the HA-SAM hydrogel. It was observed that viability of the primary keratinocytes (FIG. 2A) and fibroblasts (FIG. 2B) was high following resuspension in the HA-SAM hydrogel and UV cross-linking. Cells remained 92-98% viable following gel encapsulation.

Figure 3:
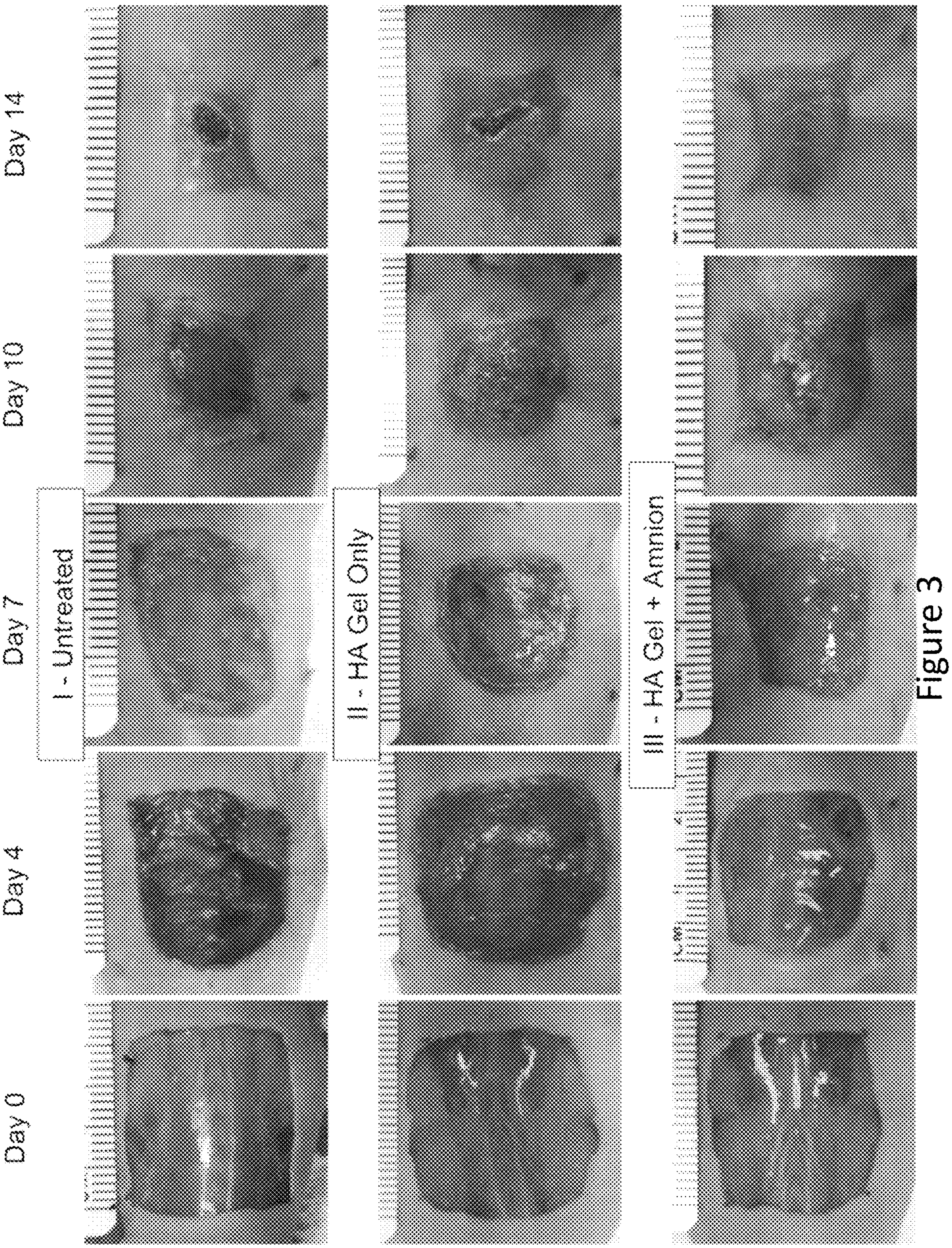
FIG. 3 is a series of images illustrating the time course of wound healing induced by different treatment. Group I was untreated, other than standard bandage. Group II was treated with a hyaluronic acid (HA)-hydrogel. Group III was treated with a HA gel comprising amnion (SAM).
Figure 4A:
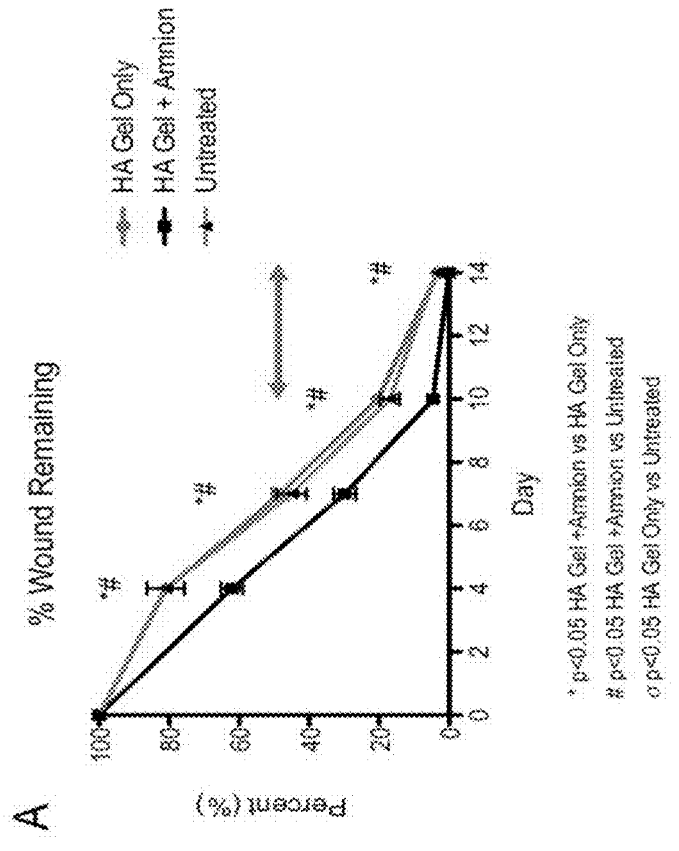
FIGS. 4A-4D depict the results of experiments illustrating the characteristics of wound healing in wounds left untreated, treated with a HA-hydrogel, or treated with a HA gel comprising SAM.
Figure 4B:
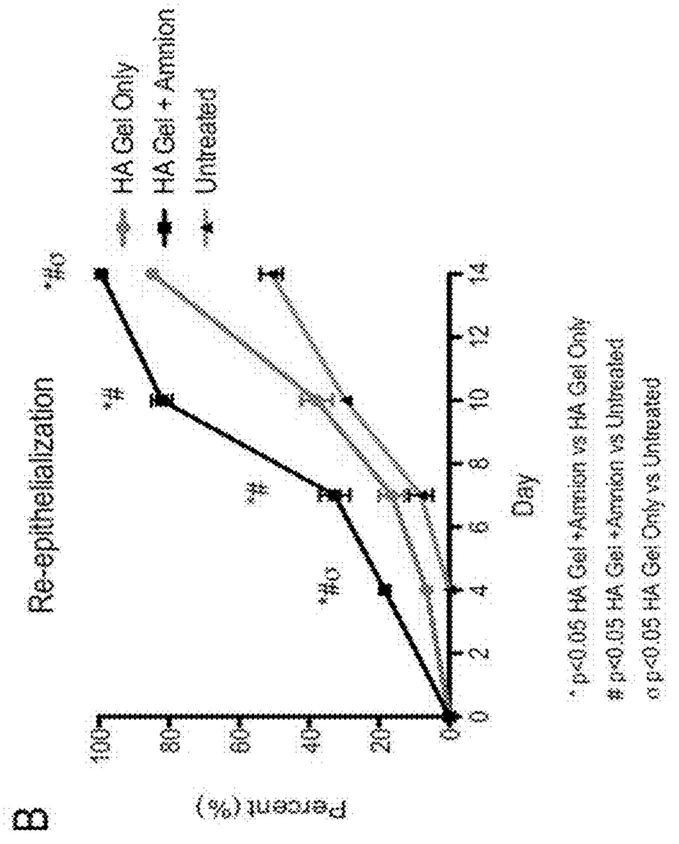
Figure 4C:
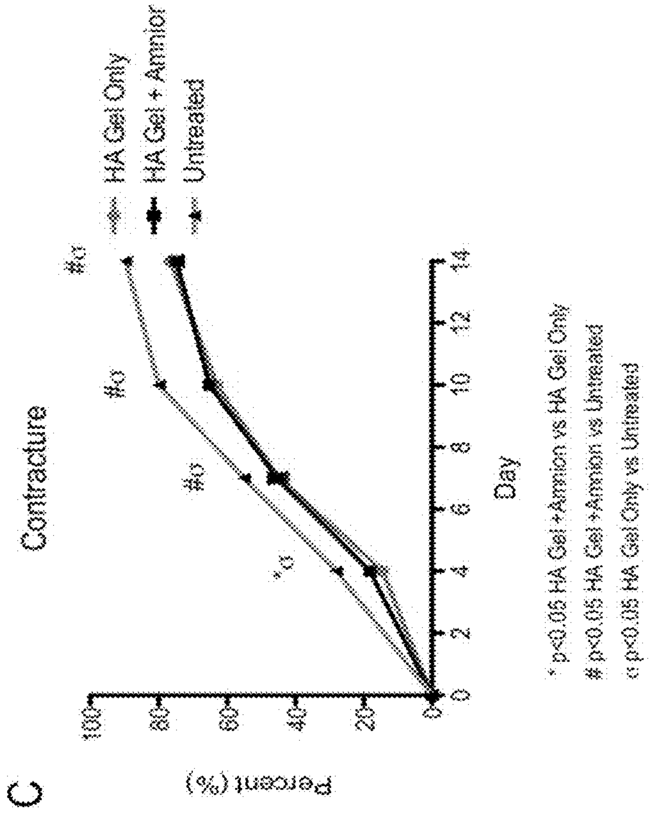
Figure 4D:
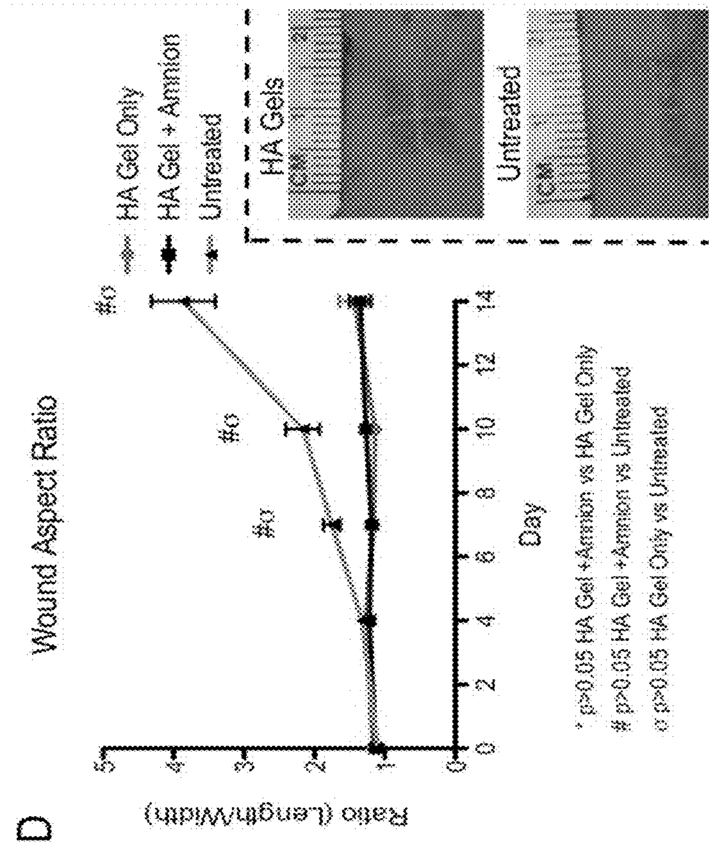
Figure 7:
FIG. 7 depicts a set of representative images of wound healing in the porcine study. Full thickness 4.0×4.0 cm skin wounds were created on the dorsal flanks of Yorkshire pigs and divided into the following groups 1) Untreated; 2) Amnion powder; 3) HA gel+amnion (HA-SAM); 4) 3M Patch; 5) Amniograft®; 6) GraftJacket®. The 3M patch refers to an electrospun experimental composition. Amnion Powder and HA-SAM-treated groups showed significant acceleration in wound healing and re-epithelialization as well as a reduction in contraction compared to control groups.

An in vivo wound healing study was performed to evaluate the efficacy of the HA-SAM hydrogel. A 2 cm by 2 cm full-thickness wound was created on the back of nude mice. Each wounded mouse received one of 3 treatment options; (1) Untreated other than standard bandage, (2) HA-gel only, or (3) HA-SAM gel. Time-course images of the wounds are depicted in FIG. 3. Gross morphology of the wounds demonstrates accelerated wound closure times and reduced contraction in the HA-SAM groups. Percentage (%) wound remaining was calculated by dividing the area of the remaining wound by the original wound size. HA-SAM groups had significant acceleration of wound closure times resulting in wound closure 3-4 days before other groups (FIG. 4A). Wound re-epithelialization was calculated by measuring newly re-epithelized skin, taking into consideration remaining wound area and contraction. HA-SAM groups had significantly greater wound re-epithelialization at all timepoints compared to other groups (FIG. 4B). Contracture was measured based on original wound size and the area of re-epithelized skin. HA-gel only and HA-SAM groups had significantly less contracture compared to untreated animals (FIG. 4C). Wound aspect ratio was determined to describe observed changes in the shape and direction of wound contraction between groups. HA-gel only and HA-SAM groups displayed symmetrical contraction, with aspect ratios close to 1, while other groups showed asymmetrical contraction with aspect ratios closer to 4 (FIG. 4D). In the porcine study, HA-SAM and amnion powder-treated groups showed accelerated wound healing, re-epithelialization and reduced contraction compared to untreated, commercially available and experimental groups (FIG. 7).

Figures 5A, 5B, 5C:
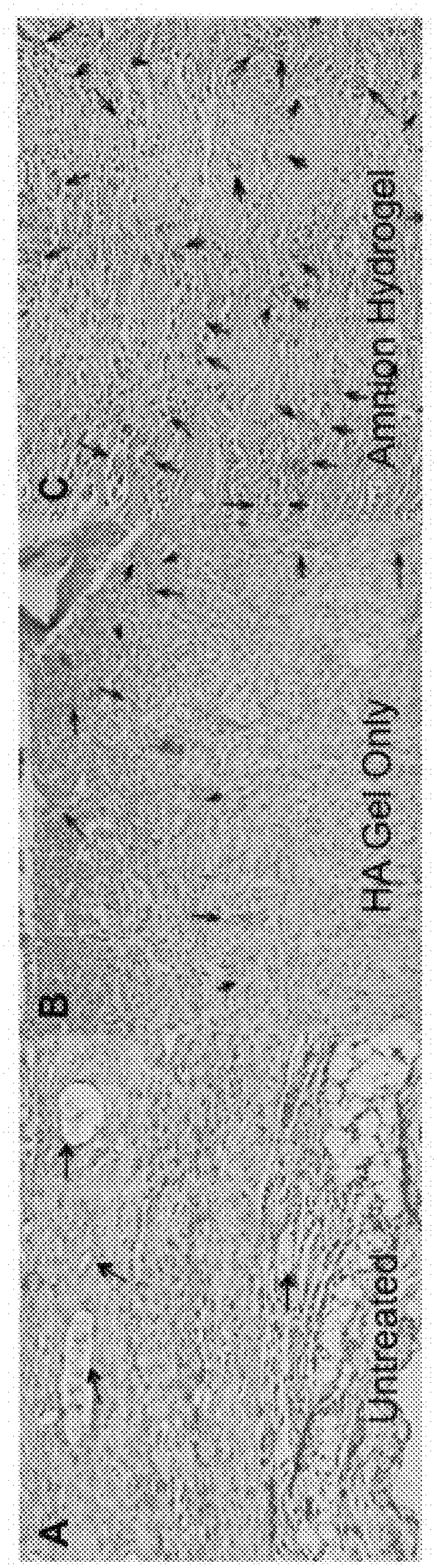
FIGS. 5A-5F depict the results of experiments.
Figure 5D:
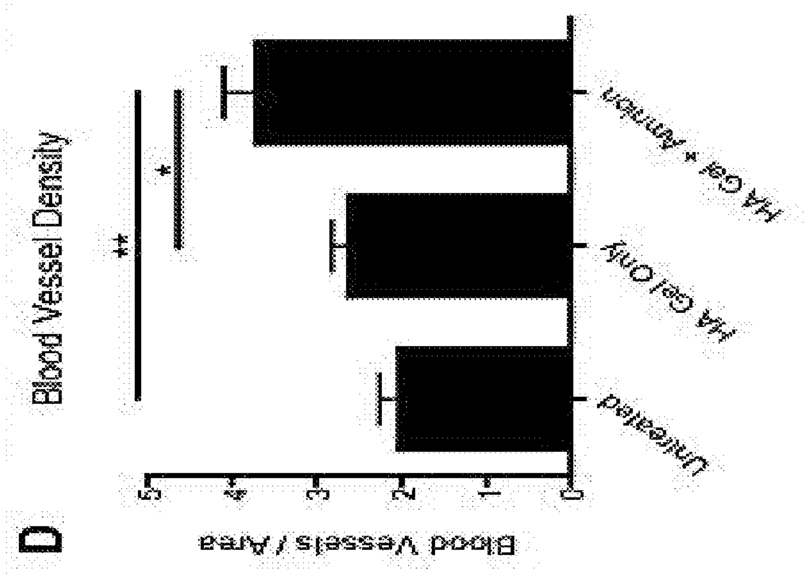
Figure 5E:
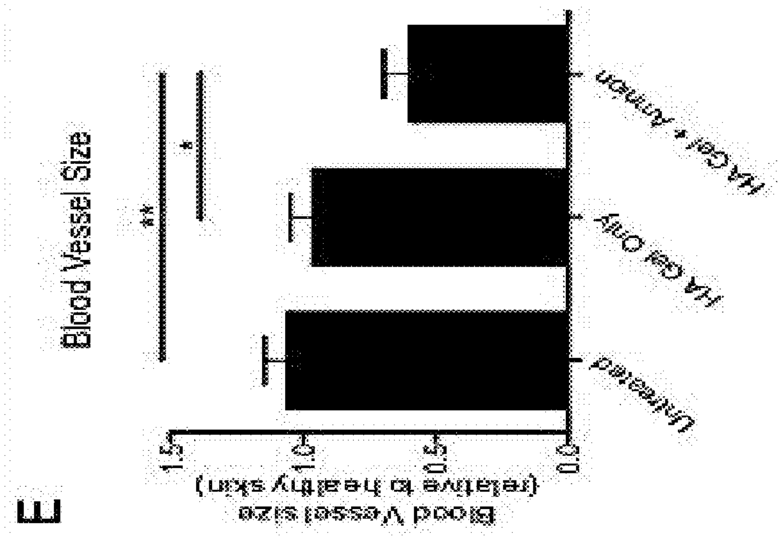
Figure 5F:
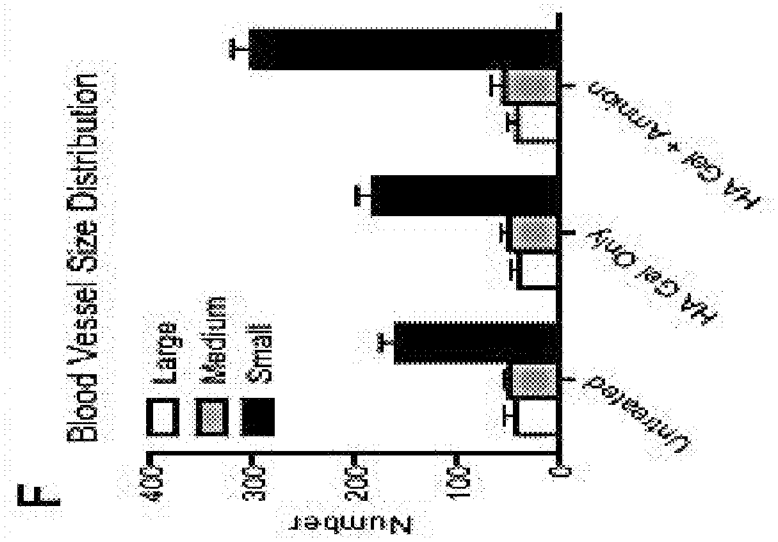

Wound area sections were subjected to hematoxylin and eosin stain (H&E stain) to detect blood vessels within the tissue. As shown in FIG. 5, there were significantly more blood vessels in HA-SAM-treated animal compared to HA-gel only and untreated groups. Blood vessel density within areas of regenerated skin was quantified by counting performed on 6 representative fields of view (FIG. 5D), which demonstrated increased density for HA-SAM treated animals compared to both untreated and HA-gel only groups. The blood vessel area was calculated and represented as relative to blood vessel size within healthy skin of the same mouse (FIG. 5E). Average blood vessel size was significantly smaller in HA-SAM-treated animal compared to HA-gel only and untreated groups. The distribution of blood vessels between large, medium and small vessels was determined, which demonstrated that the HA-SAM-treated skin has similar numbers of large and medium vessels, but significantly more smaller blood vessels, suggesting new blood vessel formation (FIG. 5F).

Blood vessels in regenerating skin were subjected to immuno-fluorescent staining for α-smooth muscle actin (αSMA) and von willebrand factor (vWF). It was observed that HA-SAM samples have significantly more blood vessels than other groups and these blood vessels appeared smaller in size than vessels within skin from other groups (FIG. 6A-6C). The epidermis of the animals were subject to immuno-fluorescent staining for keratin 10, to detect epidermis, and Ki-67, to detect proliferating cells (FIG. 6D-6F). Significantly more proliferating cells were identified near the epidermis of HA-SAM-treated animals compared to HA-gel only-treated and untreated groups (arrows). In untreated groups proliferating cells were also identified within the dermis, while this was rare in HA-gel only and HA-SAM groups.

Figure 8B:
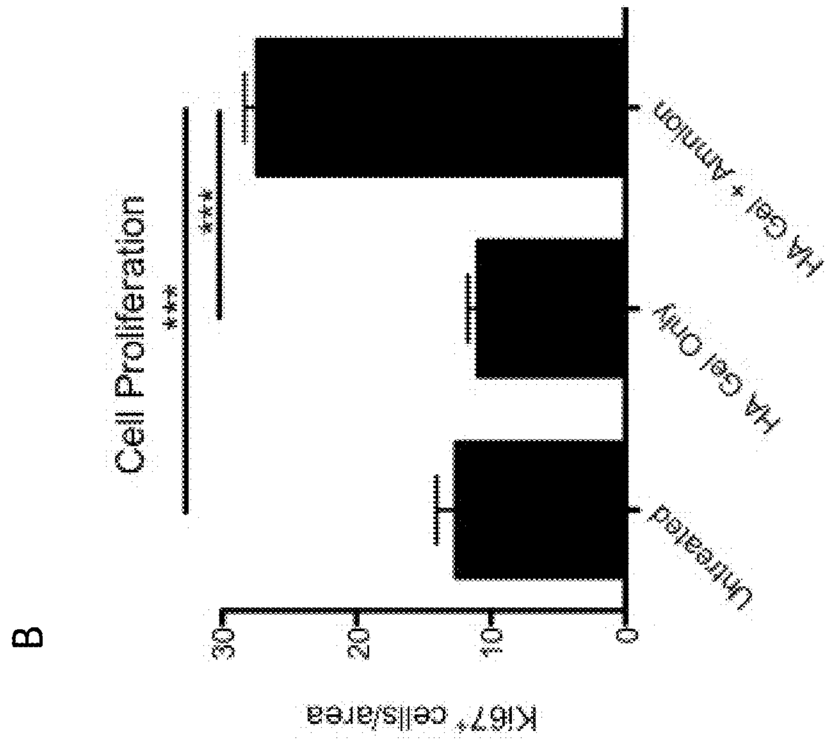
FIGS. 8A-8B depict the results of experiments.
Figure 8A:
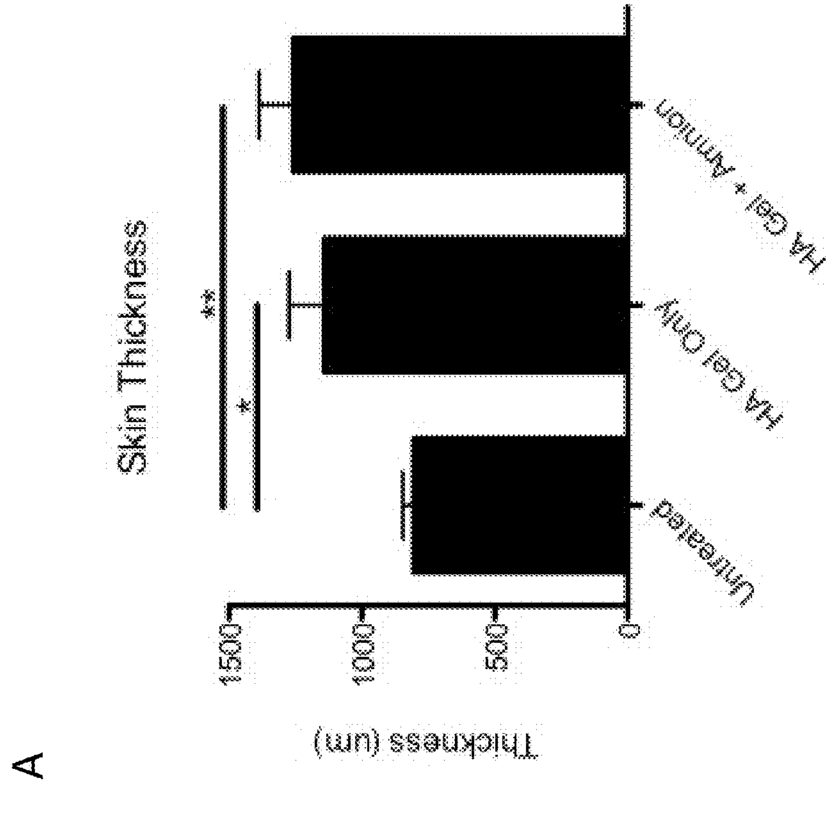

The skin thickness and cell proliferation were also examined in HA-treated and HA-SAM treated animals, compared to untreated skin. It was observed that overall skin thickness was greater for HA-treated and HA-SAM-treated animals compared to untreated skin (FIG. 8A). Further, a greater number of proliferating Ki67-positive cells were counted in HA-SAM-treated skin than in HA-treated and untreated skin (FIG. 8B).

Figures 9A, 9B, 9C, 9D, 9E:
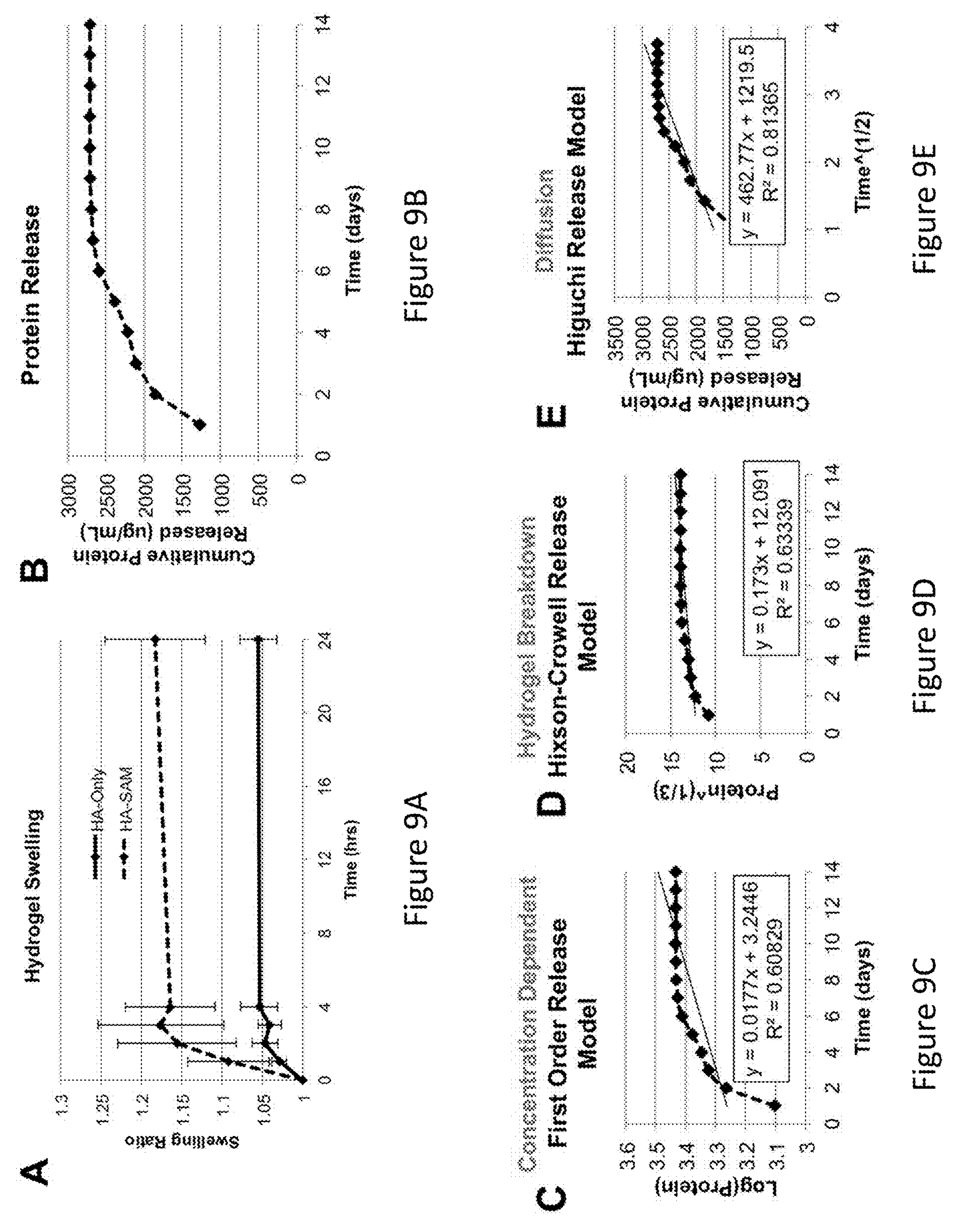
FIGS. 9A-9E depict the results of experiments.

Hydrogel swelling was compared between HA hydrogel and HA-SAM hydrogels. No significant swelling was measured for either HA hydrogel or the HA-SAM hydrogel submerged in saline solution (FIG. 9A). This suggests that the hydrogels will not absorb or release significant amounts of liquid once applied to a wound.

Experiments were conducted to evaluate protein release from the hydrogel. Protein release from the HA-SAM hydrogel was observed over a 14 day time period demonstrating the controlled and extended release of factors over time (FIG. 9B). Kinetic models of protein release were fit to the observed cumulative protein release to investigate the mechanism of protein release. Release kinetic models fit to the cumulative protein release indicate that release is primarily dominated by diffusion kinetics through a complex physical matrix (FIG. 9C-9E). First order release model analyzing concentration dependent protein release has a low $R^2$ value (FIG. 9C). Hixson-Crowell release model analyzing protein release due to hydrogel degradation shows an increased, but still low $R^2$ value (FIG. 9D). Higuchi release model analyzing protein release due to diffusion has an increase $R^2$ value, indicating a better mechanistic fit (FIG. 9E).

Figure 10:
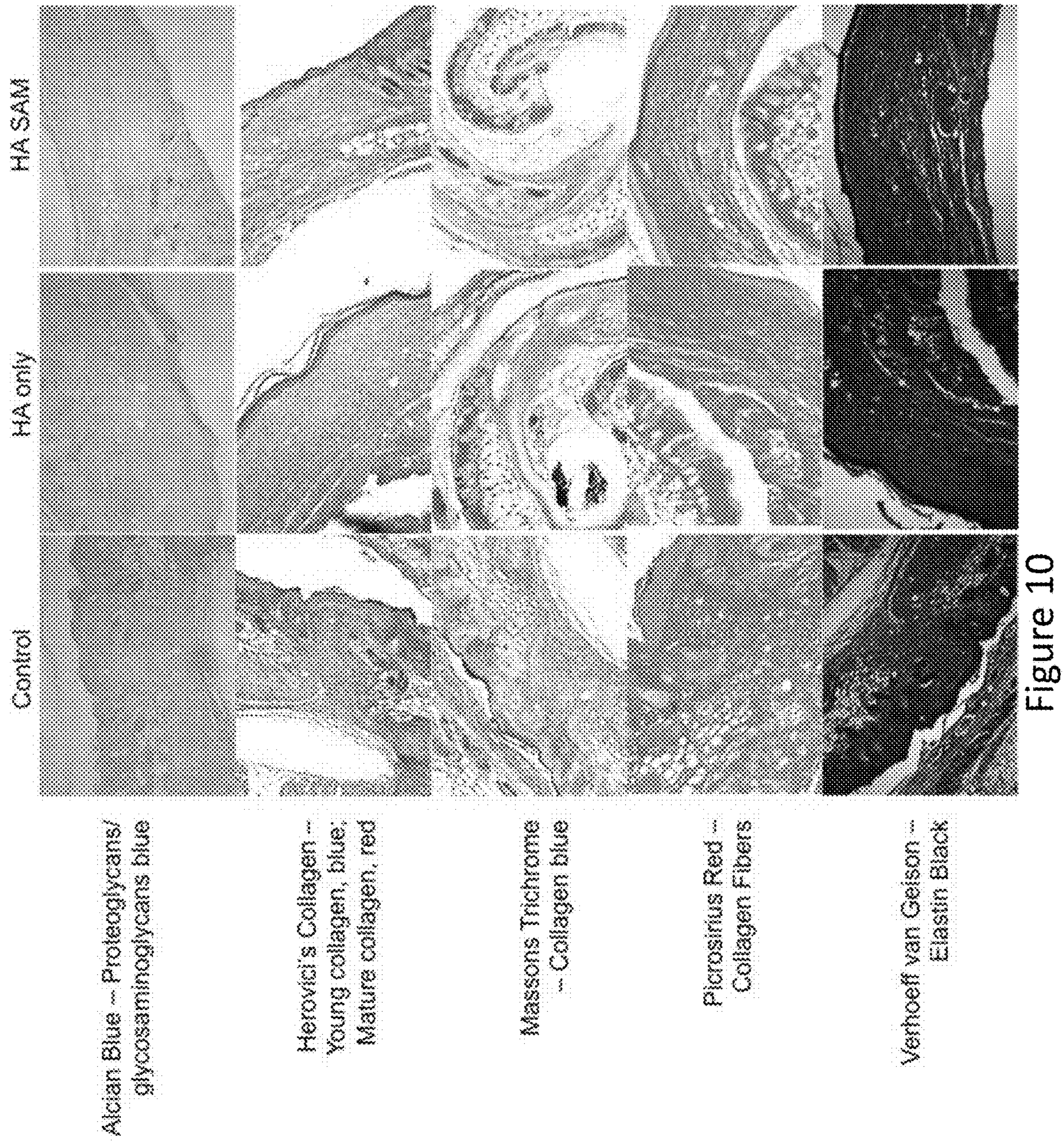
FIG. 10 is a set of images depicting the results of experiments. Images depict the staining of untreated control and of wounds treated with either HA only hydrogels or HA-SAM hydrogels. Specimens were stained with Alcian Blue, Herovici's Collagen, Massons Trichrome, Picrosirius Red, and Verhoeff van Geison.

Wounds untreated (control), or treated with HA-hydrogels or HA-SAM hydrogels were subjected to histochemical staining of various stains (FIG. 10). Herovici's Collagen Stain, Massons Trichrome and Picrosirius Red staining suggested that HA-treated and HA-SAM-treated skin had modified collagen types, maturity and distribution compared to untreated skin, suggesting reduced scarring and skin maturation. Alcian Blue and Verhoeff van Geison staining also revealed differences in elastin, proteoglycan and glycosaminoglycan composition between the groups.

Collectively, the data presented herein demonstrate that HA-SAM hydrogels effectively treats wounds. Keratinocytes and fibroblasts that were encapsulated in the gel retained over 95% viability after crosslinking. In vitro studies demonstrated that SAM increased primary keratinocyte and fibroblast proliferation and migration. In the mouse skin wound model, re-epithelialization occurred at faster rates in the HA-SAM-treated mice, resulting in a significantly faster wound healing compared to the other groups. In addition, HA-SAM and HA-only-treated wounds showed decreased wound contraction with an aspect ratio close to 1.0 compared to the control wounds that contracted more linearly with aspect ratios between 3.0 and 4.0. Histology revealed that HA-SAM-treated regenerated skin contained a significantly higher blood vessel density and greater numbers of proliferating keratinocytes within the epidermal layer. The data presented herein demonstrate that HA-SAM hydrogels is an effective cell-free treatment for skin wounds.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of making an amniotic membrane powder, the method comprising the steps of:

a) storing a placenta at 4° C. prior to separating amnion membrane and chorion membrane of the placenta;
b) cutting the amnion membrane into a plurality of pieces;
c) washing the plurality of pieces with sterile saline;
d) washing the plurality of pieces with sterile water;
e) storing the plurality of pieces at about −80° C.;
f) lyophilizing the plurality of pieces; and
g) milling the plurality of pieces to obtain the amniotic membrane powder.

2. The method of claim 1, wherein the separating comprises manually dissecting amnion membrane from chorion membrane and removing blood clots from the separated amnion membrane.

3. The method of claim 1, wherein the amnion membrane is rinsed prior to cutting.

4. The method of claim 3, wherein the rinsing comprises washing the amnion membrane with sterile saline.

5. The method of claim 4, wherein the rinsing comprises washing the amnion membrane with about 500-1000 ml sterile saline.

6. The method of claim 1, wherein each of the plurality of pieces is about 5×5 cm in size.

7. The method of claim 1, wherein the plurality of pieces is stored at −80° C. for about 12-24 hours.

8. The method of claim 1, wherein the lyophilizing is performed for about 48-72 hours.

9. The method of claim 1, wherein the milling is performed in the presence of liquid nitrogen.

10. The method of claim 1, wherein the amnion membrane powder is further treated with pepsin and irradiated with gamma radiation.

11. The method of claim 10, wherein the amniotic membrane powder is further solubilized to obtain solubilized amniotic membrane (SAM), wherein solubilizing comprises the steps of:

i. digesting the amniotic membrane powder in presence of an acid,
ii. centrifuging the digested solution and removing a supernatant;
iii. neutralizing the supernatant with a base to the pH of about 7, and
iv. storing the neutralized supernatant at about −80° C.

12. A method of making an amniotic membrane powder, the method comprising the steps of:

a) separating amnion membrane and chorion membrane of a placenta;
b) cutting the amnion membrane into a plurality of pieces;
c) washing the plurality of pieces with sterile saline;
d) washing the plurality of pieces with sterile water;
e) storing the plurality of pieces at about −80° C.;
f) lyophilizing the plurality of pieces; and
g) milling the plurality of pieces to obtain the amniotic membrane powder.

13. The method of claim 12, wherein the amnion membrane is rinsed prior to cutting.

14. The method of claim 13, wherein the rinsing comprises washing the amnion membrane with sterile saline.

15. The method of claim 14, wherein the rinsing comprises washing the amnion membrane with about 500-1000 ml sterile saline.

16. The method of claim 12, wherein each of the plurality of pieces is about 5×5 cm in size.

17. The method of claim 12, wherein the plurality of pieces is stored at −80° C. for about 12-24 hours.

18. The method of claim 12, wherein the lyophilizing is performed for about 48-72 hours.

19. The method of claim 12, wherein the milling is performed in the presence of liquid nitrogen.

* * * * *